US009986969B2

(12) United States Patent
Call et al.

(10) Patent No.: US 9,986,969 B2
(45) Date of Patent: Jun. 5, 2018

(54) ULTRASOUND IMAGING SYSTEM MEMORY ARCHITECTURE

(71) Applicant: Maui Imaging, Inc., Sunnyvale, CA (US)

(72) Inventors: Josef R. Call, Campbell, CA (US); Kenneth D. Brewer, Santa Clara, CA (US); Viet Nam Le, San Jose, CA (US); Matthew Ouellette, Menlo Park, CA (US); Mathias Blake, Madison, WI (US)

(73) Assignee: MAUI IMAGING, INC., Sunnyvale, CA (US)

(*) Notice: Subject to any disclaimer, the term of this patent is extended or adjusted under 35 U.S.C. 154(b) by 96 days.

(21) Appl. No.: 13/971,689

(22) Filed: Aug. 20, 2013

(65) Prior Publication Data
US 2014/0058266 A1   Feb. 27, 2014

Related U.S. Application Data

(60) Provisional application No. 61/691,717, filed on Aug. 21, 2012.

(51) Int. Cl.
A61B 8/14    (2006.01)
A61B 8/08    (2006.01)
(Continued)

(52) U.S. Cl.
CPC ............ A61B 8/14 (2013.01); A61B 8/4427 (2013.01); A61B 8/4483 (2013.01); A61B 8/485 (2013.01);
(Continued)

(58) Field of Classification Search
USPC ......................................................... 600/448
See application file for complete search history.

(56) References Cited

U.S. PATENT DOCUMENTS 3,174,286 A    3/1965   Erickson
3,895,381 A    7/1975   Kock
(Continued)

FOREIGN PATENT DOCUMENTS

CN    1781460       6/2006
CN    101116622 A   2/2008
(Continued)

OTHER PUBLICATIONS

Hendee et al.; Medical Imaging Physics; Wiley-Liss, Inc. 4th Edition; Chap. 19-22; pp. 303-353; © 2002 (year of pub. sufficiently earlier than effective US filing date and any foreign priority date).
(Continued)

Primary Examiner — Joel F Brutus
(74) Attorney, Agent, or Firm — Shay Glenn LLP

(57) ABSTRACT

A multiple aperture ultrasound imaging system may be configured to store raw, un-beamformed echo data. Stored echo data may be retrieved and re-beamformed using modified parameters in order to enhance the image or to reveal information that was not visible or not discernible in an original image. Raw echo data may also be transmitted over a network and beamformed by a remote device that is not physically proximate to the probe performing imaging. Such systems may allow physicians or other practitioners to manipulate echo data as though they were imaging the patient directly, even without the patient being present. Many unique diagnostic opportunities are made possible by such systems and methods.

11 Claims, 7 Drawing Sheets

(51) Int. Cl.
  *G01S 15/89* (2006.01)
  *G10K 11/34* (2006.01)
  *G01S 7/52* (2006.01)
  *A61B 8/00* (2006.01)
(52) U.S. Cl.
  CPC ............ *A61B 8/5207* (2013.01); *A61B 8/585* (2013.01); *G01S 7/52063* (2013.01); *G01S 7/52074* (2013.01); *G01S 7/52098* (2013.01); *G01S 15/8927* (2013.01); *G01S 15/8993* (2013.01); *G01S 15/8995* (2013.01); *G01S 15/8997* (2013.01); *G10K 11/346* (2013.01); *A61B 8/565* (2013.01); *A61B 8/582* (2013.01); *A61B 8/587* (2013.01); *G01S 7/52042* (2013.01); *G01S 7/52049* (2013.01); *G01S 15/8979* (2013.01)

(56) References Cited

U.S. PATENT DOCUMENTS

| | | |
|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,180,792 A | 12/1979 | Lederman et al. |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kande et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 5,050,588 A | 9/1991 | Grey et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,349,960 A | 9/1994 | Gondo |
| 5,355,888 A | 10/1994 | Kendall |
| 5,381,794 A | 1/1995 | Tei et al. |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,951,479 A * | 9/1999 | Holm .................. G01S 7/52046 600/443 |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sepia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,370,480 B1 | 4/2002 | Gupta et al. |

(56) References Cited

U.S. PATENT DOCUMENTS

| | | | |
|---|---|---|---|
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,508,770 B1 * | 1/2003 | Cai .................. G01S 7/5209 600/447 |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,865,140 B2 | 3/2005 | Thomenius et al. |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,293,462 B2 | 11/2007 | Lee et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cal |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,277,383 B2 | 10/2012 | Specht |
| 8,279,705 B2 | 10/2012 | Choi et al. |
| 8,412,307 B2 | 4/2013 | Willis et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,532,951 B2 | 9/2013 | Roy et al. |
| 8,582,848 B2 | 11/2013 | Funka-Lea et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0006266 A1 * | 1/2004 | Ustuner .................. A61B 8/08 600/407 |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236217 A1 | 11/2004 | Cerwin et al. |
| 2004/0236223 A1 | 11/2004 | Barnes et al. |
| 2005/0004449 A1 | 1/2005 | Mitschke et al. |
| 2005/0053305 A1 | 3/2005 | Li et al. |

(56) References Cited

U.S. PATENT DOCUMENTS

| | | |
|---|---|---|
| 2005/0054910 A1 | 3/2005 | Tremblay et al. |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1* | 5/2005 | Gritzky ............... A61B 8/00 600/437 |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262291 A1 | 11/2006 | Hess et al. |
| 2006/0262961 A1 | 11/2006 | Holsing et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182233 A1 | 7/2009 | Wodnicki |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0191110 A1 | 7/2010 | Insana et al. |
| 2010/0217124 A1 | 8/2010 | Cooley |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0268503 A1* | 10/2010 | Specht ............... A61B 8/00 702/104 |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | Ei-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178400 A1 | 7/2011 | Specht et al. |
| 2011/0201933 A1 | 8/2011 | Specht et al. |
| 2011/0270088 A1 | 11/2011 | Shiina |
| 2011/0301470 A1 | 12/2011 | Sato et al. |

(56) References Cited

U.S. PATENT DOCUMENTS

| | | |
|---|---|---|
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0057428 A1 | 3/2012 | Specht et al. |
| 2012/0085173 A1 | 4/2012 | Papadopoulos et al. |
| 2012/0095343 A1 | 4/2012 | Smith et al. |
| 2012/0095347 A1 | 4/2012 | Adam et al. |
| 2012/0101378 A1 | 4/2012 | Lee |
| 2012/0114210 A1 | 5/2012 | Kim et al. |
| 2012/0116226 A1 | 5/2012 | Specht |
| 2012/0121150 A1 | 5/2012 | Murashita |
| 2012/0137778 A1 | 6/2012 | Kitazawa et al. |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0035595 A1 | 2/2013 | Specht |
| 2013/0070062 A1 | 3/2013 | Fouras et al. |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0131516 A1 | 5/2013 | Katsuyama |
| 2013/0144165 A1 | 6/2013 | Ebbini et al. |
| 2013/0144166 A1 | 6/2013 | Specht et al. |
| 2013/0172743 A1 | 7/2013 | Brewer et al. |
| 2013/0204136 A1 | 8/2013 | Duric et al. |
| 2013/0204137 A1 | 8/2013 | Roy et al. |
| 2013/0218012 A1 | 8/2013 | Specht et al. |
| 2013/0247350 A1 | 9/2013 | Specht et al. |
| 2013/0253325 A1 | 9/2013 | Call et al. |
| 2013/0258805 A1 | 10/2013 | Hansen et al. |
| 2013/0261463 A1 | 10/2013 | Chiang et al. |
| 2014/0086014 A1 | 3/2014 | Kobayashi |
| 2014/0243673 A1 | 8/2014 | Anand et al. |
| 2015/0374345 A1 | 12/2015 | Specht et al. |
| 2016/0095579 A1 | 4/2016 | Smith et al. |
| 2016/0157833 A1 | 6/2016 | Smith et al. |
| 2016/0256134 A1 | 9/2016 | Specht et al. |

FOREIGN PATENT DOCUMENTS

| | | |
|---|---|---|
| CN | 101190134 A | 6/2008 |
| CN | 101453955 A | 6/2009 |
| CN | 101843501 A | 9/2010 |
| CN | 102018533 A | 4/2011 |
| CN | 102123668 | 7/2011 |
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 1462819 B1 | 7/2011 |
| EP | 2356941 A1 | 8/2011 |
| EP | 1979739 | 10/2011 |
| EP | 2385391 A2 | 11/2011 |
| EP | 2294400 | 2/2012 |
| EP | 2453256 A2 | 5/2012 |
| EP | 1840594 B1 | 6/2012 |
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | S49-11189 A | 1/1974 |
| JP | S54-44375 A | 4/1979 |
| JP | S55-103839 A | 8/1980 |
| JP | 57-31848 A | 2/1982 |
| JP | 58-223059 A | 12/1983 |
| JP | 59-101143 A | 6/1984 |
| JP | S59-174151 A | 10/1984 |
| JP | S60-13109 U | 1/1985 |
| JP | S60-68836 A | 4/1985 |
| JP | 2-501431 A | 5/1990 |
| JP | 03015455 A | 1/1991 |
| JP | 03126443 A | 5/1991 |
| JP | 04017842 A | 1/1992 |
| JP | 4-67856 | 3/1992 |
| JP | 05-042138 A | 2/1993 |
| JP | 6-125908 A | 5/1994 |
| JP | 7-051266 A | 2/1995 |
| JP | 07204201 A | 8/1995 |
| JP | 08154930 A | 6/1996 |
| JP | 08-252253 | 10/1996 |
| JP | 9-103429 A | 4/1997 |
| JP | 9-201361 A | 8/1997 |
| JP | 2777197 B | 5/1998 |
| JP | 10-216128 A | 8/1998 |
| JP | 11-089833 A | 4/1999 |
| JP | 11-239578 A | 9/1999 |
| JP | 2001-507794 A | 6/2001 |
| JP | 2001-245884 A | 9/2001 |
| JP | 2002-209894 A | 7/2002 |
| JP | 2002-253548 A | 9/2002 |
| JP | 2002-253549 A | 9/2002 |
| JP | 2004-167092 A | 6/2004 |
| JP | 2004-215987 | 8/2004 |
| JP | 2004-337457 | 12/2004 |
| JP | 2004-351214 | 12/2004 |
| JP | 2005046192 A | 2/2005 |
| JP | 2005152187 A | 6/2005 |
| JP | 2005-523792 | 8/2005 |
| JP | 2005-526539 | 9/2005 |
| JP | 2006051356 A | 2/2006 |
| JP | 2006-61203 A | 3/2006 |
| JP | 2006-122657 A | 5/2006 |
| JP | 2006130313 A | 5/2006 |
| JP | 2007-325937 A | 12/2007 |
| JP | 2008-122209 | 5/2008 |
| JP | 2008-513763 A | 5/2008 |
| JP | 2008132342 A | 6/2008 |
| JP | 2008522642 A | 7/2008 |
| JP | 2008-259541 A | 10/2008 |
| JP | 2008279274 A | 11/2008 |
| JP | 2009240667 A | 10/2009 |
| JP | 20105375 | 1/2010 |
| JP | 2010124842 A | 6/2010 |
| JP | 2010526626 A | 8/2010 |
| KR | 100715132 B | 4/2007 |
| KR | 1020090103408 A | 10/2009 |
| WO | WO 92/18054 A1 | 10/1992 |
| WO | WO 98/00719 A2 | 1/1998 |
| WO | WO01/64109 A1 | 9/2001 |
| WO | WO02/084594 A2 | 10/2002 |
| WO | WO2005/009245 A1 | 2/2005 |
| WO | WO 2006/114735 A1 | 11/2006 |
| WO | WO 2007/127147 A2 | 11/2007 |
| WO | WO2009/060182 A2 | 5/2009 |
| WO | WO 2010/017445 A2 | 2/2010 |
| WO | WO 2010/095094 A1 | 8/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |

(56) References Cited

FOREIGN PATENT DOCUMENTS

| WO | WO2012/160541 A2 | 11/2012 |
|---|---|---|
| WO | WO2013/059358 A2 | 4/2013 |
| WO | WO2013/109965 A1 | 7/2013 |
| WO | WO2013/116807 A1 | 8/2013 |
| WO | WO2013/116809 A1 | 8/2013 |
| WO | WO2013/116851 A1 | 8/2013 |
| WO | WO2013/116854 A1 | 8/2013 |
| WO | WO2013/116866 A1 | 8/2013 |
| WO | WO2013/128301 A2 | 9/2013 |

OTHER PUBLICATIONS

Wikipedia; Point cloud; 2 pages; retrieved Nov. 24, 2014 from the internet (https://en.wikipedia.org/w/index.php?title=Point_cloud&oldid=472583138).
Smith et al.; U.S. Appl. No. 14/526,186 entitled "Universal multiple aperture medical ultrasound probe," filed Oct. 28, 2014.
Smith et al.; U.S. Appl. No. 14/595,083 entitled "Concave ultrasound transducers and 3D arrays," filed Jan. 12, 2015.
Li et al.; An efficient speckle tracking algorithm for ultrasonic imaging; 24; pp. 215-228; Oct. 1, 2002.
UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.
Wikipedia; Curve fitting; 5 pages; retrieved from the internet (http:en.wikipedia.org/wiki/Curve_fitting) Dec. 19, 2010.
Specht et al.; U.S. Appl. No. 14/279,052 entitled "Ultrasound imaging using apparent point-source transmit transducer," filed May 15, 2014.
Wikipedia; Speed of sound; 17 pages; retrieved from the internet (http:en.wikipedia.org/wiki/Speed_of_sound) Feb. 15, 2011.
Specht; U.S. Appl. No. 14/754,422 entitled "Method and apparatus to produce ultrasonic images using multiple apertures," filed Jun. 29, 2015.
Cristianini et al.; An Introduction to Support Vector Machines; Cambridge University Press; pp. 93-111; Mar. 2000.
Du et al.; User parameter free approaches to multistatic adaptive ultrasound imaging; 5th IEEE International Symposium; pp. 1287-1290, May 2008.
Feigenbaum, Harvey, M.D.; Echocardiography; Lippincott Williams & Wilkins; Philadelphia; 5th Ed.; pp. 428, 484; Feb. 1994.
Haykin, Simon; Neural Networks: A Comprehensive Foundation (2nd Ed.); Prentice Hall; pp. 156-187; Jul. 16, 1998.
Kramb et al.,; Considerations for using phased array ultrasonics in a fully automated inspection system. Review of Quantitative Nondestructive Evaluation; vol. 23, ed. D. O. Thompson and D. E. Chimenti, pp. 817-825, (year of publication is sufficiently earlier than the effective U.S. filing date and any foreign priority date) 2004.
Ledesma-Carbayo et al.; Spatio-temporal nonrigid registration for ultrasound cardiac motion estimation; IEEE Trans. On Medical Imaging; vol. 24; No. 9; Sep. 2005.
Leotta et al.; Quantitative three-dimensional echocardiography by rapid imaging . . . ; J American Society of Echocardiography; vol. 10; No. 8; ppl 830-839; Oct. 1997.
Morrison et al.; A probabilistic neural network based image segmentation network for magnetic resonance images; Proc. Conf. Neural Networks; Baltimore, MD; vol. 3; pp. 60-65; Jun. 1992.
Nadkarni et al.; Cardiac motion synchronization for 3D cardiac ultrasound imaging; Ph.D. Dissertation, University of Western Ontario; Jun. 2002.
Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.
Sakas et al.; Preprocessing and volume rendering of 3D ultrasonic data; IEEE Computer Graphics and Applications; pp. 47-54, Jul. 1995.
Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.
Sapia et al.; Ultrasound image deconvolution using adaptive inverse filtering; 12 IEEE Symposium on Computer-Based Medical Systems, CBMS, pp. 248-253; Jun. 1999.
Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.
Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.
Specht et al.; Deconvolution techniques for digital longitudinal tomography; SPIE; vol. 454; presented at Application of Optical Instrumentation in Medicine XII; pp. 319-325; Jun. 1984.
Specht et al.; Experience with adaptive PNN and adaptive GRNN; Proc. IEEE International Joint Conf. on Neural Networks; vol. 2; pp. 1203-1208; Orlando, FL; Jun. 1994.
Specht, D.F.; A general regression neural network; IEEE Trans. on Neural Networks; vol. 2.; No. 6; Nov. 1991.
Specht, D.F.; Blind deconvolution of motion blur using LMS inverse filtering; Lockheed Independent Research (unpublished); Jun. 23, 1975.
Specht, D.F.; Enhancements to probabilistic neural networks; Proc. IEEE International Joint Conf. on Neural Networks; Baltimore, MD; Jun. 1992.
Specht, D.F.; GRNN with double clustering; Proc. IEEE International Joint Conf. Neural Networks; Vancouver, Canada; Jul. 16-21, 2006.
Specht, D.F.; Probabilistic neural networks; Pergamon Press; Neural Networks; vol. 3; pp. 109-118; Feb. 1990.
Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.
Wells, P.N.T.; Biomedical ultrasonics; Academic Press; London, New York, San Francisco; pp. 124-125; Mar. 1977.
Widrow et al.; Adaptive signal processing; Prentice-Hall; Englewood Cliffs, NJ; pp. 99-116; Mar. 1985.
Belevich et al.; U.S. Appl. No. 13/964,701 entitled "Calibration of Multiple Aperture Ultrasound Probes," filed Aug. 12, 2013.
Smith et al.; U.S. Appl. No. 14/210,015 entitled "Alignment of ultrasound transducer arrays and multiple aperture probe assembly," filed Mar. 13, 2014.
Abeysekera et al.; Alignment and calibration of dual ultrasound transducers using a wedge phantom; Ultrasound in Medicine and Biology; 37(2); pp. 271-279; Feb. 2011.
Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb. 28, 2008.
Chen et al.; Maximum-likelihood source localization and unknown sensor location estimation for wideband signals in the near-field; IEEE Transactions on Signal Processing; 50(8); pp. 1843-1854; Aug. 2002.
Chen et al.; Source localization and tracking of a wideband source using a randomly distributed beamforming sensor array; International Journal of High Performance Computing Applications; 16(3); pp. 259-272; Fall 2002.
Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.
Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.
Heikkila et al.; A four-step camera calibration procedure with implicit image correction; Proceedings IEEE Computer Scociety

(56) References Cited

OTHER PUBLICATIONS

Conference on Computer Vision and Pattern Recognition; San Juan; pp. 1106-1112; Jun. 17-19, 1997.
Hsu et al.; Real-time freehand 3D ultrasound calibration; CUED/F-INFENG/TR 565; Department of Engineering, University of Cambridge, United Kingdom; 14 pages; Sep. 2006.
Jeffs; Beamforming: a brief introduction; Brigham Young University; 14 pages; retrieved from the internet (http://ens.ewi.tudelft.nl/Education/courses/et4235/Beamforming.pdf); Oct. 2004.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.
Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Urban et al; Implementation of vibro-acoustography on a clinical ultrasound system; IEEE Transactions on Ultrasonics, Ferroelectrics, and Frequency Control; 58(6); pp. 1169-1181 (Author Manuscript, 25 pgs.); Jun. 2011.
Urban et al; Implementation of vibro-acoustography on a clinical ultrasound system; IEEE Ultrasonics Symposium (IUS); pp. 326-329; Oct. 14, 2010.
Wang et al.; Photoacoustic tomography of biological tissues with high cross-section resolution: reconstruction and experiment; Medical Physics; 29(12); pp. 2799-2805; Dec. 2002.
Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.
Brewer et al.; U.S. Appl. No. 15/005,866 entitled "M-mode ultrasound imaging of arbitrary paths," filed Jan. 25, 2016.
Specht; U.S. Appl. No. 15/240,884 entitled "Method and apparatus to produce ultrasonic images using multiple apertures," filed Aug. 18, 2016.
Arigovindan et al.; Full motion and flow field recovery from echo doppler data; IEEE Transactions on Medical Imaging; 26(1); pp. 31-45; Jan. 2007.
Capineri et al.; A doppler system for dynamic vector velocity maps; Ultrasound in Medicine & Biology; 28(2); pp. 237-248; Feb. 28, 2002.
Dunmire et al.; A brief history of vector doppler; Medical Imaging 2001; International Society for Optics and Photonics; pp. 200-214; May 30, 2001.
Saad et al.; Computer vision approach for ultrasound doppler angle estimation; Journal of Digital Imaging; 22(6); pp. 681-688; Dec. 1, 2009.
Zang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.
Specht et al.; U.S. Appl. No. 15/364,075 entitled "Point source transmission and speed-of-sound correction using multi-aperture ultrasound imaging," filed Nov. 29, 2016.
Smith et al.; U.S. Appl. No. 15/364,092 entitled "Alignment of ultrasound transducer arrays and multiple aperture probe assembly," filed Nov. 29, 2016.
Specht et al.; U.S. Appl. No. 14/078,311 entitled "Imaging with Multiple Aperture Medical Ultrasound and Synchronization of Add-On Systems," filed Nov. 12, 2013.
Specht, D. F.; U.S. Appl. No. 14/157,257 entitled "Method and Apparatus to Produce Ultrasonic Images Using Multiple Apertures," filed Jan. 16, 2014.

* cited by examiner

ULTRASOUND IMAGING SYSTEM MEMORY ARCHITECTURE

CROSS-REFERENCE TO RELATED APPLICATIONS

This application claims the benefit of U.S. Provisional Patent Application No. 61/691,717, filed on Aug. 21, 2012, titled "Ultrasound Imaging System Memory Architecture", the contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to ultrasound imaging systems and more particularly to ultrasound imaging systems that make use of raw echo data memory devices.

BACKGROUND

In conventional ultrasonic imaging, a focused beam of ultrasound energy is transmitted into body tissues to be examined and the returned echoes are detected and plotted to form an image. While ultrasound has been used extensively for diagnostic purposes, conventional ultrasound has been greatly limited by depth of scanning, speckle noise, poor lateral resolution, obscured tissues and other such problems.

In order to insonify body tissues, an ultrasound beam is typically formed and focused either by a phased array or a shaped transducer. Phased array ultrasound is a commonly used method of steering and focusing a narrow ultrasound beam for forming images in medical ultrasonography. A phased array probe has many small ultrasonic transducer elements, each of which can be pulsed individually. By varying the timing of ultrasound pulses (e.g., by pulsing elements one by one in sequence along a row), a pattern of constructive interference is set up that results in a beam directed at a chosen angle. This is known as beam steering. Such a steered ultrasound beam may then be swept through the tissue or object being examined. Data from multiple beams are then combined to make a visual image showing a slice through the object.

Traditionally, the same transducer or array used for transmitting an ultrasound beam is used to detect the returning echoes. This design configuration lies at the heart of one of the most significant limitations in the use of ultrasonic imaging for medical purposes: poor lateral resolution. Theoretically, the lateral resolution could be improved by increasing the width of the aperture of an ultrasonic probe, but practical problems involved with aperture size increase have kept apertures small. Unquestionably, ultrasonic imaging has been very useful even with this limitation, but it could be more effective with better resolution.

SUMMARY OF THE DISCLOSURE

A method of ultrasound imaging is provided, comprising the steps of transmitting an unfocused ping ultrasound pulse with a multiple aperture imaging system to insonify a region of interest, generating in real-time a first image of a first section of the region of interest, storing echo data received from the insonified region in a memory device, after the storing step, retrieving the echo data from the memory device, and processing the echo data to form a second image of a second section of the region of interest, wherein the second section covers a portion of the region of interest not present first section.

In some embodiments, the generating step comprises using a first set of beamforming parameters, and the processing step comprises using a second set of beamforming parameters different than the first set of beamforming parameters.

In one embodiment, the second image has a higher pixel resolution than the first image. In another embodiment, the second image covers a portion of the region of interest within the first section. In some embodiments, the first and second sections of the region of interest are entirely non-overlapping.

In some embodiments, the method further comprises processing the echo data to form a third image of a third section of the region of interest, wherein the third image covers a portion of the region of interest not present in the second image, and simultaneously displaying the second image and the third image.

In some embodiments, a cross-section of a human heart is visible in the first image, only a first portion of the heart is visible in the second image, and only a second portion of the heart is visible in the third image.

In some embodiments, forming a second image and forming a third image further comprise combining a plurality of image layers, each image layer corresponding to a different combination of a transmitted ultrasound pulse and a receive aperture, and wherein forming the second image comprises combining a different number of image layers than forming the third image.

In one embodiment, the method further comprises measuring an object visible in the second image.

A method of processing ultrasound data is also provided, comprising the steps of retrieving a first data set from a first non-volatile digital memory device, the first data set comprising position and orientation information of a transmit aperture, retrieving a second data set from a second non-volatile digital memory device, the second data set comprising a series of ultrasound echo strings, each ultrasound echo string comprising echo data associated with a transmit aperture responsible for producing the echo data, determining a transmit location of the transmit aperture from the first data set, determining a receive location of a receive aperture from the second data set, and beamforming the second data set using a first set of beamforming parameters to produce a first set of images of a target object.

In some embodiments, the method further comprises adjusting at least one beamforming parameter to form a second set of beamforming parameters, and beamforming the second data set using the second set of beamforming parameters to produce a second set of images of the target object.

In one embodiment, the at least one beamforming parameter is a speed-of-sound in the target object. In another embodiment, the at least one beamforming parameter is a position of a transmit transducer element of the transmit aperture or a receive transducer element of the receive aperture. In an additional embodiment, the at least one beamforming parameter is a weighting factor.

In some embodiments, the method further comprises defining an image window of the target object, and beamforming the second data set to produce a second set of images of the image window of the target object.

In some embodiments, the image window covers an area within the first set of images and less than a total area of the first set of images, the method further comprising measuring a size of a structure visible in the second set of images.

In another embodiment, the method comprises adding an m-mode line to a display based on an image formed from the second data set.

In other embodiments, the method further comprises adjusting an algorithm for combining images coherently and incoherently.

In some embodiments, producing the first set of images further comprises combining a first plurality of image layers to form a first set of frames, each image layer corresponding to a different combination of the transmit aperture and the receive aperture, and displaying the first set of frames at a first frame rate.

In other embodiments, the method comprises beamforming the second data set to produce a second set of images of the target object, including combining a second plurality of image layers to form a second set of frames, each image layer corresponding to a different combination of the transmit aperture and the receive aperture, the second set of frames having a greater number of frames than the first set of frames, and displaying the second set of frames at a second frame rate that is higher than the first frame rate.

An ultrasound imaging system is also provided, comprising a multiple aperture ultrasound probe having a plurality of transmit transducer elements and a plurality of receive transducer elements, transmit control electronics configured to control transmission of ultrasound pulses from the transmit transducer elements of the probe, receiver electronics configured to receive echo signals from the receive transducer elements corresponding to echoes of the ultrasound pulses, and a raw data memory in electronic communication with the receiver electronics, the raw data memory containing digital data representing an identity of at least one transmit element, a time at which the at least one transmit element sent an ultrasound pulse, and a series of data points representing a magnitude of echoes from the ultrasound pulse.

In some embodiments, the system comprises a beamformer in electronic communication with the raw data memory, the beamformer being configured to retrieve echo data from the raw data memory and to form images from the retrieved echo data.

An ultrasound image-processing computing device is provided, comprising a processor, a first non-volatile memory device containing process code, a second non-volatile memory device containing ultrasound echo data associated with a transmit aperture, and containing transducer element location data defining an acoustic position of transmit transducer elements of the transmit aperture relative to receive transducer elements of a receive aperture, wherein the processor is configured to execute the process code in the first non-volatile memory device to retrieve the ultrasound echo data from the second memory device, and form images by beamforming the echo data based on the transducer element location data.

In some embodiments, the device is not electronically or physically connected to an ultrasound probe containing the transmit aperture and the receive aperture.

A method of ultrasound imaging is provided, comprising transmitting an ultrasound ping from at least one transmit element into a patient, storing transmit information pertaining to the ultrasound ping in raw data memory, receiving echoes corresponding to the ultrasound ping with at least one receive element, sampling the echoes at a plurality of sampling points to generate a digital record containing a signal magnitude and timestamp entry, and storing the digital record in raw data memory for each sampling point.

In some embodiments, the method further comprises forming an ultrasound image from the digital record.

In another embodiment, the method comprises performing a calibration operation of the transmit and receive elements to obtain updated calibration data, and processing the digital record using the updated calibration data to form an ultrasound image.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
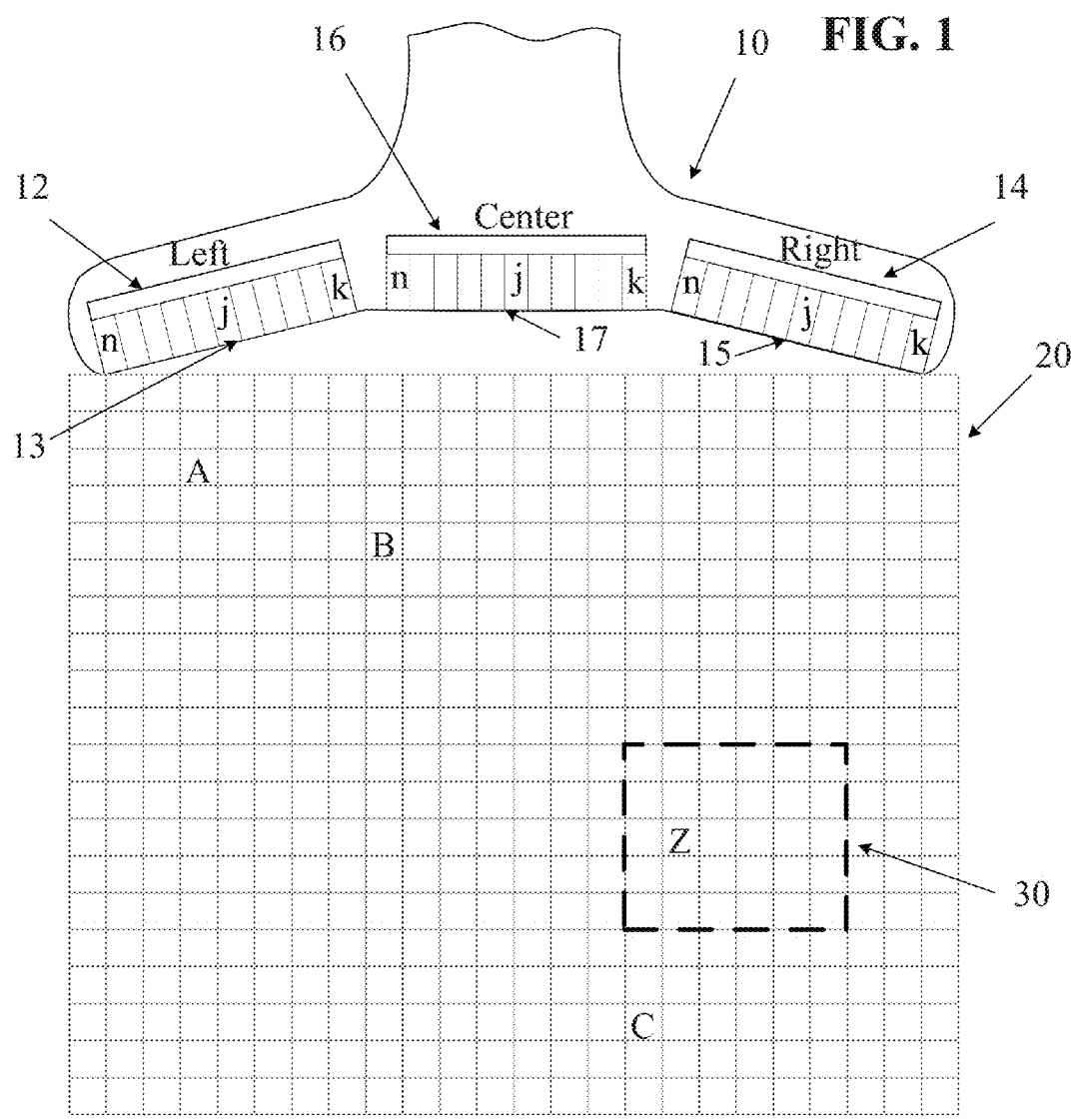
FIG. 1 is a schematic illustration of a multiple aperture ultrasound imaging probe and a grid of points to be imaged.

The various embodiments will be described in detail with reference to the accompanying drawings. References made to particular examples and implementations are for illustrative purposes, and are not intended to limit the scope of the invention or the claims.

Intro and Definitions

Although the various embodiments are described herein with reference to ultrasound imaging of various anatomic structures, it will be understood that many of the methods and devices shown and described herein may also be used in other applications, such as imaging and evaluating non-anatomic structures and objects. For example, the probes, systems and methods described herein may be used in non-destructive testing or evaluation of various mechanical objects, structural objects or materials, such as welds, pipes, beams, plates, pressure vessels, layered structures, etc. The various embodiments below include systems and methods for using an ultrasound imaging system that is configured to store raw, un-beamformed ultrasound data for subsequent beamforming and processing into image data. Such a system enables many unique methods of using ultrasound imaging systems.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In some other embodiments, ultrasound transducers may comprise capacitive micromachined ultrasound transducers (CMUT).

Transducers are often configured in arrays of multiple individual transducer elements. As used herein, the terms "transducer array" or "array" generally refers to a collection of transducer elements mounted to a common backing plate. Such arrays may have one dimension (1D), two dimensions (2D), 1.X dimensions (1.XD) or three dimensions (3D). Other dimensioned arrays as understood by those skilled in the art may also be used. Annular arrays, such as concentric circular arrays and elliptical arrays may also be used. An element of a transducer array may be the smallest discretely functional component of an array. For example, in the case of an array of piezoelectric transducer elements, each element may be a single piezoelectric crystal or a single machined section of a piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" may refer to a conceptual "opening" through which ultrasound signals may be sent and/or received. In actual practice, an aperture is simply a single transducer element or a group of transducer elements that are collectively managed as a common group by imaging control electronics. For example, in some embodiments an aperture may be a physical grouping of elements which may be physically separated from elements of an adjacent aperture. However, adjacent apertures need not necessarily be physically separated.

It should be noted that the terms "receive aperture," "insonifying aperture," and/or "transmit aperture" are used herein to mean an individual element, a group of elements within an array, or even entire arrays with in a common housing, that perform the desired transmit or receive function from a desired physical viewpoint or aperture. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures.

As used herein, the term "total aperture" refers to the total cumulative size of all imaging apertures. In other words, the term "total aperture" may refer to one or more dimensions defined by a maximum distance between the furthest-most transducer elements of any combination of send and/or receive elements used for a particular imaging cycle. Thus, the total aperture is made up of any number of sub-apertures designated as send or receive apertures for a particular cycle. In the case of a single-aperture imaging arrangement, the total aperture, sub-aperture, transmit aperture, and receive aperture will all have the same dimensions. In the case of a multiple array probe, the dimensions of the total aperture may include the sum of the dimensions of all of the arrays.

In some embodiments, two apertures may be located adjacent one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

Elements and arrays described herein may also be multi-function. That is, the designation of transducer elements or arrays as transmitters in one instance does not preclude their immediate redesignation as receivers in the next instance. Moreover, embodiments of the control system herein include the capabilities for making such designations electronically based on user inputs, pre-set scan or resolution criteria, or other automatically determined criteria.

As used herein the term "point source transmission" or "ping" may refer to an introduction of transmitted ultrasound energy into a medium from a single spatial location. This may be accomplished using a single ultrasound transducer element or combination of adjacent transducer elements transmitting together as a single transmit aperture. A single transmission from a point source transmit aperture approximates a uniform spherical wave front, or in the case of imaging a 2D slice, a uniform circular wave front within the 2D slice. In some cases, a single transmission of a circular or spherical wave front from a point source transmit aperture may be referred to herein as a "ping" or a "point source pulse."

As used herein, the phrase "pixel resolution" refers to a measure of a number of pixels in an image, and may be expressed with two positive integers, the first referring to a number of pixel columns (image width) and the second referring to a number of pixel rows (image height). Alternatively, pixel resolution may be expressed in terms of a total number of pixels (e.g., the product of the number of rows and the number of columns), a number of pixels per unit length, or a number of pixels per unit area. "Pixel resolution" as used herein is distinct from other uses of the term "resolution" which refers to the level of detail visible in an image. For example, "lateral resolution" may refer to the level of detail that may be discerned along a horizontal axis in an ultrasound image plane, independent of how an image of such a plane may be represented as a digital image made up of pixels.

Ping-Based Ultrasound Imaging

In various embodiments, point-source transmission ultrasound imaging, otherwise referred to as ping-based ultrasound imaging, provides several advantages over traditional scanline-based imaging. Point source transmission differs in its spatial characteristics from a "phased array transmission" which focuses energy in a particular direction from the transducer element array along a directed scanline. An un-focused point source pulse (ping) may be transmitted so as to generate a circular (or spherical) wavefront in the scanning plane, thereby insonifying as wide an area as possible. Echoes from scatterers in the region of interest will return to all of the elements of receive apertures. Those echo signals may be filtered, amplified, digitized and stored in short term or long term memory (depending on the needs or capabilities of a particular system).

Images may then be reconstructed from received echoes by assuming that the wavefronts emitted from the point source are physically circular in the region of interest. In actuality, the wavefront will also have some penetration in the dimension normal to the scanning plane (i.e., some energy may essentially "leak" into the dimension perpendicular to the desired two-dimensional scanning plane, reducing the effective imaging reach). Additionally, the "circular" wavefront may actually be limited to a semicircle or a fraction of a circle less than 180 degrees ahead of the front face of the transducer according to the unique off-axis properties of a transducing material. Similarly, when transmitting three-dimensional "spherical" wavefronts, such wavefronts may actually have a shape of a semi-sphere or less, depending on characteristics of the transmit element(s) used.

The process of forming an image from received echoes is generally referred to herein as "beamforming." In ping-based imaging, beamforming may generally involve determining a pixel display location for each received echo sample. Because each ping insonifies an entire imaged region, a "complete" (albeit blurry) image may be formed with the echoes of a single transducer element. An image that may be formed from echoes received by a single receive transducer element may be referred to as a sub-image. The image quality may be improved by combining the sub-images formed from echoes received at a plurality of transducer elements. Transducer elements may be grouped into "apertures," and sub-images from elements of a common aperture may be combined to form an image layer.

Beamforming of ping-based echoes may be performed using a software-based or hardware-based dynamic beamforming technique, in which a beamformer's focus may be continuously changed to focus at a particular pixel position as that pixel is being imaged. Such a beamformer may be used to plot the position of echoes received from a point source pulse. In some embodiments, a dynamic beamformer may plot the locus of each echo signal based on a round-trip travel time of the signal from the transmitter to an individual receive transducer element.

The locus of a single reflector will lie along an ellipse with a first focus at the position of the transmit transducer element(s) and the second focus at the position of the receive transducer element. Although several other possible reflectors lie along the same ellipse, echoes of the same reflector will also be received by each of the other receive transducer elements of a receive aperture. The slightly different positions of each receive transducer element means that each receive element will define a slightly different ellipse for a given reflector. Accumulating the results by coherently summing the ellipses for all elements of a common receive aperture will indicate an intersection of the ellipses for a reflector, thereby converging towards a point at which to display a pixel representing the reflector. The echo amplitudes received by any number of receive elements may thereby be combined into each pixel value. In other embodiments the computation can be organized differently to arrive at substantially the same image.

Various algorithms may be used for combining echo signals received by separate receive elements. For example, some embodiments may process echo-signals individually, plotting each echo signal at all possible locations along its ellipse, then proceeding to the next echo signal. Alternatively, each pixel location may be processed individually, identifying and processing all echoes potentially contributing to that pixel location before proceeding to the next pixel location.

Image quality may be further improved by combining images formed by the beamformer from one or more subsequent transmitted pings, transmitted from the same or a different point source (or multiple different point sources). Still further improvements to image quality may be obtained by combining images formed by more than one receive aperture. The process of combining separately beamformed images may generally referred to herein as image layer combining. Combining images from echoes received at multiple, separate apertures of a multiple aperture ultrasound probe may further improve image quality.

In some embodiments, ping-based multiple aperture imaging may operate by transmitting a point-source ping from a first transmit aperture and receiving echoes with elements of two or more receive apertures, one or more of which may include some or all elements of a transmit aperture. An image may be formed by triangulating the position of scatterers based on delay times between ping transmission and reception of echoes, the speed of sound, and the relative positions of transmit and receive transducer elements. As a result, a sub-image of the entire insonified region may be formed from echoes of each transmitted ping received by each receive element. Combining sub-images from echoes received by multiple elements grouped into a single receive aperture may produce the improvement described above with reference to intersecting ellipses.

In some embodiments, a single time domain frame may be formed by combining images formed from echoes received at two or more receive apertures from a single transmitted ping. In other embodiments, a single time domain frame may be formed by combining images formed from echoes received at one or more receive apertures from two or more transmitted pings. In some such embodiments, the multiple transmitted pings may originate from different transmit apertures. FIG. 1 illustrates an embodiment of a three-array multiple aperture ultrasound imaging probe 10 and a region of interest 20 to be imaged represented as a grid. The probe 10 is shown with a left transducer array 12 which may include three transmit apertures labeled 'n,' 'j,' and 'k' (which may be referred to herein by short-hand designations Ln, Lj and Lk). A right transducer array 14 may also include three transmit apertures 'n,' 'j,' and 'k' (which may be referred to herein by short-hand designations Rn, Rj and Rk). Some or all of the elements of the left transducer array 12 may also be designated as a left receive aperture 13. Similarly, some or all of the elements of the right transducer array 14 may be designated as a right receive aperture 15. In addition to the left and right arrays, a multiple aperture ultrasound probe 10 may include a center transducer array 16, which may include three transmit apertures labeled 'n,' 'j,' and 'k' (which may be referred to herein by short-hand designations Cn, Cj and Ck). Some or all of the elements of the center transducer array 16 may also be designated as a center receive aperture 17. It should be understood that each of the three apertures can include any number of transducer elements which may be spaced from one another in one, two or three dimensions.

In other embodiments, any other multiple aperture ultrasound imaging probe may be used in connection with the systems and methods described below.

In some embodiments, the width of a receive aperture may be limited by the assumption that the speed of sound is the same for every path from a scatterer to each element of the receive aperture. In a narrow enough receive aperture this simplifying assumption is acceptable. However, as receive aperture width increases, an inflection point is reached (referred to herein as the "maximum coherent aperture width," "maximum coherent width" or "coherence width") at which the echo return paths will necessarily pass though different types of tissue having different speeds of sound. When this difference results in phase shifts approaching 180 degrees, additional receive elements beyond the maximum coherent receive aperture width will actually degrade the image rather than improve it.

Therefore, in order to make use of a wide probe with a total aperture width greater than the maximum coherent width, the full probe width may be physically or logically divided into multiple apertures, each of which may be limited to a width less than the maximum coherent aperture width for an intended imaging application and small enough to avoid phase cancellation of received signals. The maximum coherent width can be different for different patients and for different probe positions on the same patient. In some embodiments, a compromise width may be determined for a given imaging scenario. In other embodiments, a multiple aperture ultrasound imaging control system may be configured with a dynamic algorithm to subdivide the available elements in multiple apertures into groups that are small enough to avoid significant phase cancellation.

In some embodiments, it may be difficult or impossible to meet additional design constraints while grouping elements into apertures with a width less than the maximum coherent width. For example, if material is too heterogeneous over very small areas, it may be impractical to form apertures small enough to be less than the maximum coherent width. Similarly, if a system is designed to image a very small target at a substantial depth, an aperture with a width greater than the maximum coherent width may be needed. In such cases, a receive aperture with a width greater than the maximum coherent width can be accommodated by making additional adjustments, or corrections may be made to account for differences in the speed-of-sound along different paths. Some examples of such speed-of-sound adjustments are provided here, while other methods may also be known.

Image Layer Combining

As described above, multiple image layers may be combined to improve the overall quality of a final combined image. In some embodiments, the number of image layers can be the product of the number of receive apertures and the number of transmit apertures (where a "transmit aperture" can be a single transmit element or a group of transmit elements). In other embodiments, the same ping imaging processes may also be performed using a single receive aperture. In some embodiments, some image layer combining may be performed prior to beamforming. In such embodiments, two or more sets of echoes may be combined coherently or incoherently (as discussed below), and a beamforming process may be performed using the result of such a combination. Such pre-beamform image layer combining may be used to combine echo data corresponding to sub-images that may be formed from echoes received by multiple elements of a common receive aperture. Alternatively, such pre-beamform image layer combining may be used to combine echo data corresponding to sub-images that may be formed from in-phase and quadrature echo data received by a single receive element.

In one embodiment with reference to FIG. 1, a first image layer (e.g., representing all points in the grid 20, or only sections of the grid 20) may be constructed by transmitting a first ping from a first transmit aperture Ln, receiving echoes of the first ping with the elements of a left receive aperture 13, and combining sub-images constructed from echoes received by each element of the left receive aperture 13. In some embodiments, sub-images may be coherently combined to form an image layer. A second image layer may be similarly formed from echoes of the first ping received with the elements of the right receive aperture 15. Third and fourth image layers may be similarly formed by transmitting a second ping from a second transmit aperture Lj and receiving echoes of the second ping with the elements of the left receive aperture 13 and with the elements of the right receive aperture 15. In some embodiments, all four image layers may then be combined to form a single time domain image frame. In other embodiments, a single time domain image frame may be obtained from echoes received at any number of receive apertures and/or from any number of pings transmitted by any number of transmit apertures. Time domain image frames may then be displayed sequentially on a display screen as a continuous moving image. Still images may also be formed by combining image layers using any of the above techniques.

Display screens and the images displayed on them may generally be divided into a grid of pixels. In some cases, a pixel is the smallest individually controllable area of a display screen. Relationships between image pixels and display pixels are generally well understood in the art, and will not be described here. For the purposes of the present description, the square cells of the grids 20 shown in the figures will be referred to as pixels. In many of the embodiments herein, groups of pixels may be treated together as a common group. Thus, the use of the term "pixel" is not intended to be limited to any particular size, but is used as a convenient term for describing a discrete section of an image.

Unless otherwise specified, the grid 20 of FIG. 1 simultaneously represents a grid of display pixels and a grid of corresponding points within a region of interest ("ROI") in an object being imaged. The term "ROI points" will be used herein to describe points within the scan plane (or 3D scan volume) at fixed locations relative to the probe. As will become clear from the following description, ROI points will not necessarily always correlate directly to pixel locations. For example, if an image is "zoomed in" to represent a smaller area 30, the grid of display pixels 20 would correspond only to the points within the zoomed area 30 in the region of interest. However, at any zoom level, the physical location of an ROI point represented by a given image pixel may be determined (relative to the probe) with a high degree of accuracy.

With a multiple aperture probe using a point-source transmission imaging technique, each image pixel may be assembled by beamforming received echo data to combine information from echoes received at each of the multiple receive apertures and transmitted from each of the multiple transmit apertures. In some embodiments of ping-based multiple aperture imaging, receive beamforming may comprise forming a pixel of a reconstructed image by summing time-delayed echoes returned by a scatterer in the object being examined and received by receive transducer elements. The time delays corresponding to such echoes may be correlated with pixel locations based on the geometry of the probe elements (i.e., the position of each element relative to a common coordinate system) and an assumed value for the speed of sound through the medium being imaged. An important consideration is whether the summation should be coherent (phase sensitive) or incoherent (summing the magnitude of the signals while disregarding the phase information). In general, sub-images constructed from echoes received by two or more individual receive elements grouped into a common receive aperture may be combined using coherent summation.

Summation of image layers resulting from multiple transmitted pings may be accomplished either by coherent addition, incoherent addition, or a combination of the two. Coherent addition (retaining phase information during addition of magnitudes) tends to maximize lateral resolution, whereas incoherent addition (summing the magnitude of the signals without considering the phase information) tends to reduce speckle noise and also minimize the effects of image layer mis-alignment errors that may be caused by minor variations in the speed of sound through the imaged medium. Speckle noise is reduced through incoherent summing because each image layer will tend to develop its own independent speckle pattern and summing the patterns incoherently has the effect of averaging out the speckle patterns; on the other hand, if the patterns are added coherently only one strong speckle pattern results.

Variations in the speed of sound are tolerated by incoherent addition because summing two pixels coherently with a speed-of-sound variation resulting in only half a wavelength's delay can result in destructive phase cancellation; whereas if they are added incoherently the same or greater delay causes only an insignificant distortion in the image layer. The addition of such image layers may result in some smoothing of the final image (in some embodiments, such smoothing may be added intentionally to make the image more readable).

Image layer combining may be described in terms of three image layer levels for which the determination of coherent vs. incoherent summing can be made. These three cases include first-level image layers, second-level image layers and third-level image layers. (1) A first-level image layer may be formed from echoes received at a single receive aperture resulting from a single ping from a single transmit aperture. For a unique combination of a single ping and a single receive aperture, the sub-images from echoes received by all the receive elements in the receive aperture may be summed to obtain a first-level image layer. (2) Multiple first-level image layers resulting from echoes of multiple transmitted pings (from the same or different transmit apertures) received at a single receive aperture can be summed together to produce a second-level image layer. Second-level image layers may be further improved by additional processing to improve alignment or other image characteristics. (3) Third-level images may be obtained by combining second-level image layers formed with data from multiple different receive apertures. In some embodiments, third-level images may be displayed as sequential time-domain frames to form a moving image video.

At all three image layer levels coherent addition can lead to maximum lateral resolution of a multiple aperture system if the geometry of the probe elements is known to a desired degree of precision and the assumption of a substantially constant speed of sound across all paths is valid. Likewise, at all image layer levels, incoherent addition leads to the best averaging out of speckle noise and tolerance of minor variations in speed of sound through the imaged medium.

In some embodiments, coherent addition can be used to combine image layers resulting from apertures for which phase cancellation is not likely to be a problem, and incoherent addition can then be used where phase cancellation would be more likely to present a problem, such as when combining images formed from echoes received at different receive apertures separated by a distance sufficient to cause the total aperture of the two receive apertures to exceed the coherence width for a given imaging application.

In some embodiments, all first-level images may be formed by using coherent addition assuming the receive apertures used were chosen to have a width less than the maximum coherent aperture width. For second and third level image layers, many combinations of coherent and incoherent summation are possible. For example, in some embodiments, second-level image layers may be formed by coherently summing contributing first-level image layers, while third-level image layers may be formed by incoherent summing of the contributing second-level image layers.

In other embodiments, it may be desirable to combine image layers through any of a wide variety of algorithms using combinations of coherent and incoherent summation. In some embodiments, an imaging control system may be configured to store a plurality of selectable pre-programmed summation algorithms that may be designed for specific imaging applications. In some embodiments, such stored summation algorithms may be manually selectable such as by operating a manual user interface control. Alternatively, such stored summation algorithms may be automatically selectable based on other data or information available to the control system.

For example, in some embodiments an alternative algorithm may comprise forming all second-level and third-level image layers by coherent addition. In another embodiment, all second-level and/or third-level image layers may be formed by incoherent addition. In further embodiments, only selected combinations of second-level images may be combined coherently to form third-level images. In other embodiments, only selected combinations of first-level image layers may be combined coherently to form second-level image layers.

In some embodiments, a first-level image layer may also be formed by summing in-phase and quadrature echo data (i.e., summing each echo with an echo ¼ wavelength delayed) for each receive-aperture element. In most embodiments, echoes received by elements of a single receive aperture are typically combined coherently. In some embodiments, the number of receive apertures and/or the size of each receive aperture may be changed in order to maximize some desired combination of image quality metrics such as lateral resolution, speed-of-sound variation tolerance, speckle noise reduction, etc. In some embodiments, such alternative element-to-aperture grouping arrangements may be selectable by a user. In other embodiments, such arrangements may be automatically selected or developed by an imaging system.

Once an image layer (at any level) is formed by incoherent summation of sub-images or image layers from lower levels, any phase information from the lower-level images and from the combined image layer is forever lost. Thus, any subsequent image layers using an image layer formed by incoherent summation will themselves necessarily be incoherently combined. Thus, in some embodiments, phase information may be retained for as long as desired in an image-layer combining process.

As discussed above, an average speed-of-sound value is typically assumed during beamforming in order to determine the location of specific points within the region of interest and corresponding pixels based on time delays between a transmit time and a receive time. In soft human tissue, the speed of sound is typically assumed to be about 1540 m/s. However, the speed of sound is known to vary by as much as 10% or more between patients and between different types of soft tissue within a single patient. Variation between an assumed speed-of-sound and an actual value for a particular scatterer path may cause temporal errors during beamforming, which may in turn cause a blurring effect in an image. Therefore, in some embodiments a multiple aperture ultrasound imaging system may be configured to allow for automatic and/or manual adjustment of an assumed speed of sound value for some or all scatterer paths.

In some embodiments, a multiple aperture imaging system may include a "coarse" speed-of-sound adjustment that increases or decreases an assumed value of speed-of-sound used in beamforming for all scatterer paths (i.e., for all combinations of transmit aperture and receive aperture). In some cases, such an adjustment may also be provided for single-aperture ultrasound imaging systems. A coarse speed-of-sound adjustment may be manual (e.g., a dial, slider or any other physical or virtual user interface device) to allow a sonographer or other user to directly increase or decrease an assumed speed-of-sound value until the system produces a result acceptable to the user. In other embodiments, a "coarse" speed of sound adjustment may be controlled automatically by an imaging control system. Thus, a coarse speed-of-sound adjustment may apply a single adjustment to all image layers.

Various embodiments of "fine" speed-of-sound adjustments may also be provided. In some embodiments, a fine speed-of-sound adjustment may be configured to adjust an assumed speed of sound value for a single receive aperture. In other embodiments, a fine speed-of-sound adjustment may be configured to adjust an assumed speed of sound value for a single transmit aperture. In further embodiments, a fine speed-of-sound adjustment may be configured to adjust an assumed speed of sound value for one or more specific combinations of transmit aperture and receive aperture. Thus, fine speed-of-sound controls may be configured to effectively apply adjustments to specific first-level or second-level image layers. As with coarse speed-of-sound adjustments, fine speed-of-sound adjustments may be manual, automatic or a combination of the two.

In some embodiments, a coarse speed-of-sound adjustment may be made manually by a user, and fine speed-of-sound adjustments may be made automatically by the ultrasound imaging control system. In other embodiments, both coarse and fine speed-of-sound adjustments may be automatically controlled. In some embodiments, the ultrasound imaging control system may be configured to evaluate different coarse and/or fine speed of sound values until a desired image quality metric (e.g., sharpness of edges or points, maximum contrast, maximum dynamic range, etc.) of the resulting image (or images) exceeds a threshold value. Alternatively any other "autofocus" algorithms may be applied to adjust a speed-of-sound value until an image quality metric is improved or optimized. For example, any of various error minimizing optimization processes may be used.

Ultrasound Systems with Raw Data Memory Architecture

Figure 3:
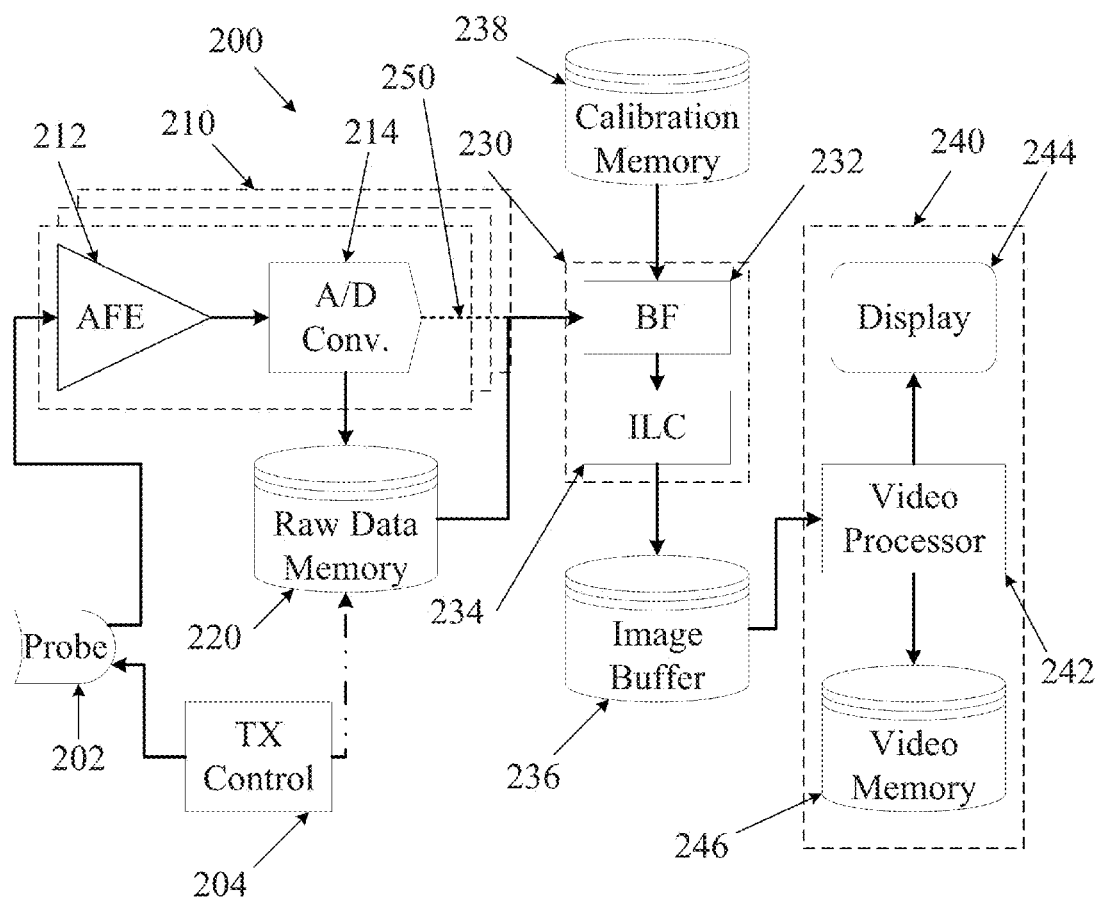
FIG. 3 is a block diagram illustrating several functional components of one embodiment of an ultrasound imaging system configured for local raw echo data capture.

FIG. 3 is a block diagram illustrating components that may be included in some embodiments of an ultrasound imaging system. The diagram of FIG. 3 includes several subsystems: a transmit control subsystem 204, a probe subsystem 202, a receive subsystem 210, an image generation subsystem 230, and a video subsystem 240. Unlike most ultrasound systems, the system of FIG. 3 provides a memory device configured to store raw un-beamformed echo data for later retrieval and processing.

As used herein, the phrases "echo data," "raw echo data" and "raw data" may refer to stored echo information describing received ultrasound echoes (RX data) at any level of processing prior to beamforming. In various embodiments, received echo data may be stored at various stages between pure analog echo signals all the way to fully processed digital images or even digital video. For example, a purely raw analog signal may be stored using an analog recording medium such as analog magnetic tape. At a slightly higher level of processing, digital data may be stored immediately after passing the analog signal through an analog-to-digital converter. Further incremental processing, such as band-pass filtering, interpolation, down-sampling, up-sampling, other filtering, etc., may be performed on the digitized echo data, and "raw" output data may be stored after such additional filtering or processing steps. Such raw data may then be beamformed to determine a pixel location for each received echo, thereby forming an image. Individual still images may be combined as frames to form motion video. In some embodiments of the systems and methods described herein, it may be desirable to store digitized echo data after performing very little processing (e.g., after some filtering and conditioning of digital echo data, but before performing any beamforming or image processing). Some ultrasound systems store beamformed echo data or fully processed image data.

In addition to received echo data, it may also be desirable to store information about one or more transmitted ultrasound signals that generated a particular set of echo data. For example, when imaging with a multiple aperture ping ultrasound method as described above, it is desirable to know information about a transmitted ping that produced a particular set of echoes. Such information may include the identity and/or position of one or more a transmit elements, as well as frequency, amplitude (magnitude), pulse length (duration), waveform (shape), or other information describing a transmitted ultrasound signal. Transmit data may be collectively referred herein to as "TX data". In some embodiments, such TX data may be stored explicitly in the same raw data memory device in which raw echo data is stored. For example, TX data describing a transmitted signal may be stored as a header before or as a footer after a set of raw echo data generated by the transmitted signal. In other embodiments, TX data may be stored explicitly in a separate memory device that is also accessible to a system performing a beamforming process. In embodiments in which transmit data is stored explicitly, the phrases "raw echo data" or "raw data" may also include such explicitly stored TX data.

TX data may also be stored implicitly. For example, if an imaging system is configured to transmit consistently defined ultrasound signals (e.g., consistent amplitude, waveform shape, frequency, pulse length, etc.) in a consistent or known sequence, then such information may be assumed during a beamforming process. In such cases, the only information that needs to be associated with the echo data is the position (or identity) of the transmit transducer(s). In some embodiments, such information may be implicitly stored and extracted based on the organization of raw echo data in a raw data memory.

For example, a system may be configured to store a fixed number of echo records following each ping. In such embodiments, echoes from a first ping may be stored at memory positions 0 through 'n' (where 'n' is the number of records stored for each ping), and echoes from a second ping may be stored at memory positions n+1 through 2n+1. In other embodiments, one or more empty or specially encoded records may be left in between echo sets. In some embodiments received echo data may be stored using various memory interleaving techniques to imply a relationship between a transmitted ping and a received echo data point (or a group of echoes). In general, a collection of echo records corresponding to echoes of a single transmitted ping received by a single receive element may be referred to herein as a single "echo string." A complete echo string may refer to all echoes of the single ping received by the receive element, whereas a partial string may refer to a sub-set of all echoes of the single ping received by the receive element.

Similarly, assuming data is sampled at a consistent, known sampling rate, the time at which each echo data point was received may be inferred from the position of that data point in memory. In some embodiments, the same techniques may also be used to implicitly store data from multiple receive channels in a single raw data memory device.

In other embodiments, the raw echo data stored in the raw data memory device 220 may be in any other structure as desired, provided that a system retrieving the echo data is able to determine which echo signals correspond to which receive transducer element and to which transmitted ping. In some embodiments, position data describing the position of each receive transducer element may be stored in the calibration memory device 238 along with information that may be linked to the echo data received by that same element. Similarly, position data describing the position of each transmit transducer element may be stored in the calibration memory device 238 along with information that may be linked to the TX data describing each transmitted ping.

In some embodiments, each echo string in the raw data memory device 220 may be associated with position data describing the position of the receive transducer element that received the echoes and with data describing the position of one or more transmit elements of a transmit aperture that transmitted the ping that produced the echoes. Each echo string may also be associated with TX data describing characteristics of the transmitted ping. Such associations may be made using any suitable data structures.

As shown in FIG. 3, an ultrasound imaging system 200 may comprise an ultrasound probe 202 which may include a plurality of individual ultrasound transducer elements, some of which may be designated as transmit elements, and others of which may be designated as receive elements. In some embodiments, each probe transducer element may convert ultrasound vibrations into time-varying electrical signals and vice versa. In some embodiments, the probe 202 may include any number of ultrasound transducer arrays in any desired configuration. A probe 202 used in connection with the systems and methods described herein may be of any configuration as desired, including single aperture and multiple aperture probes.

The transmission of ultrasound signals from elements of the probe 202 may be controlled by a transmit controller 204. In a ping-based imaging system, ultrasound signals may be transmitted as distinct, un-focused pings with characteristics selected to insonify as wide of a region as possible. As such, characteristics of each transmitted ping may be controlled. Such characteristics may include frequency, amplitude, pulse length, waveform (shape) and others. In some embodiments, all pings transmitted during an imaging session may have substantially the same characteristics while some may be transmitted from different transmit apertures. In some other embodiments, In some embodiments, a maximum frame rate of an imaging system using ping-based imaging techniques may be reached when a ping repetition frequency (i.e., the number of transmitted pings per unit time) is equal to an inverse of the round trip travel time (i.e., the time required for an ultrasound wave to travel from a transmit transducer to a reflector at a desired distance from the transducer, plus the time for an echo to return from the reflector to a receive transducer along the same or a different path).

In some embodiments it may be desirable to transmit a second ping before all echoes of a first ping have been received, a case which may be referred to as "overlapping pings". Transmitting overlapping pings may be desirable in imaging cases, such as Doppler imaging or very high frame-rate imaging, in which it may be desirable to achieve a ping repetition rate (the number of transmitted pings per unit of time) that is faster than a round-trip travel time of sound waves in the imaged medium would otherwise allow. In some embodiments, overlapping pings may be distinguished from one another using coded excitation or other methods. For example, a second ping may be transmitted before all echoes from a first ping are received if the first and second ping are transmitted with characteristics that makes it possible for an imaging system to correctly distinguish echoes as resulting from the first or the second ping. Several coded excitation techniques are known to those skilled in the art, any of which may be used with a point-source multiple aperture imaging probe. For example, pings may be frequency coded by transmitting a first ping at a first frequency and a second ping at a second (higher or lower) frequency. Echoes of such pings may then be distinguished by processing the received echoes with frequency bandpass filters tuned to extract the first frequency and the second frequency in order to isolate echoes of the first ping from echoes of the second ping.

Upon receiving echoes of transmitted signals, the probe elements may generate time-varying electric signals corresponding to the received ultrasound vibrations. Signals representing the received echoes may be output from the probe 202 and sent to a receive subsystem 210. In some embodiments, the receive subsystem may include multiple channels, each of which may include an analog front-end device ("AFE") 212 and an analog-to-digital conversion device (ADC) 214.

In some embodiments, each channel of the receive subsystem 210 may also include data conditioners and/or digital filters of various types (e.g., finite impulse response (FIR) and/or infinite impulse response (IIR) filters, real and/or complex filters, low-pass, bandpass, and/or high-pass filters with one or more center frequencies, passband widths, stopband rolloff rates, etc.), not shown, after the ADC 214. In some embodiments, analog filters prior to the ADC 214 may also be provided. The output of each ADC 214 may be directed into a raw data memory device 220. In some embodiments, an independent channel of the receive subsystem 210 may be provided for each receive transducer element of the probe 202. In other embodiments, two or more transducer elements may share a common receive channel. In still other embodiments, a single transducer element may use two or more receive channels, the output of which may be stored as two or more separate record sets in the raw data memory. For example, the raw data memory may contain two or more distinct echo strings associated with a single receive element and representing overlapping time periods.

In some embodiments, an analog front-end device 212 (AFE) may perform certain filtering processes before passing the signal to an analog-to-digital conversion device 214 (ADC). The ADC 214 may be configured to convert received analog signals into a series of digital data points at some predetermined sampling rate. Unlike most ultrasound systems, some embodiments of the ultrasound imaging system of FIG. 3 may then store digital data representing the timing, phase, magnitude and/or the frequency of ultrasound echo signals received by each individual receive element in a raw data memory device 220 before performing any further beamforming, filtering, image layer combining or other image processing.

In order to convert the captured digital samples into an image, the data may be retrieved from the raw data memory 220 by an image generation subsystem 230. As shown, the image generation subsystem 230 may include a beamforming block 232 which may form image layers by beamforming echo data, and an image layer combining ("ILC") block 234 which may combine image layers according to a desired algorithm. In some embodiments, a beamformer 232 may be in communication with a calibration memory 238 that contains probe calibration data. Probe calibration data may include information about the precise acoustic position, operational quality, and/or other information about individual probe transducer elements. The calibration memory 238 may be physically located within the probe, within the imaging system, or in a location external to both the probe and the imaging system.

In some embodiments, after passing through the image generation block 230, image data may then be stored in an image buffer memory 236 which may store beamformed and (in some embodiments) layer-combined image frames. A video processor 242 within a video subsystem 240 may then retrieve image frames from the image buffer, and may process the images into a video stream that may be displayed on a video display 244 and/or stored in a video memory 246 as a digital video clip, e.g., as referred to in the art as a "cine loop". The image processor may perform one or more conditioning or information overlay operations on the still and/or moving images prior to actual display or storage—for example, mean or Gaussian filtering, unsharp masking or edge detection, median or salt-and-pepper filtering, multiple-frame averaging (also referred to as persistence averaging in the art), data annotations, etc.

In some embodiments, the transmit controller 204 may include any combination of analog and digital components for controlling transducer elements of the probe 202 to transmit un-focused ultrasound pings at desired frequencies and intervals from selected transmit apertures according to a desired imaging algorithm. In some embodiments a transmit controller 204 may be configured to transmit ultrasound pings at a range of ultrasound frequencies, amplitudes, pulse lengths, waveforms, etc. In some (although not all) embodiments, the transmit controller may also be configured to operate as a phased array, transmitting focused (i.e., transmit beamformed) ultrasound scanline beams.

In some embodiments, the AFE 212 may be configured to perform various amplification and filtering processes to a received analog signal before passing the analog signal to an analog-to-digital conversion device. For example, an AFE 212 may include amplifiers such as a low noise amplifier (LNA), a variable gain amplifier (VGA), a bandpass filter, and/or other amplification or filtering devices. In some embodiments, an AFE device 212 may be configured to begin passing an analog signal to an ADC 214 upon receiving a trigger signal. In other embodiments, an AFE device can be "free running", continuously passing an analog signal to an ADC.

In some embodiments, each analog-to-digital converter 214 may generally include any device configured to sample a received analog signal at some consistent, predetermined sampling rate. For example, in some embodiments, an analog-to-digital converter may be configured to record digital samples of a time-varying analog signal at 25 MHz, which is 25 million samples per second or one sample every 40 nanoseconds. Thus, data sampled by an ADC may simply include a list of data points, each of which may correspond to a signal value at a particular instant. In some embodiments, an ADC 214 may be configured to begin digitally sampling an analog signal upon receiving a trigger signal. In other embodiments, an ADC device can be "free running", continuously sampling a received analog signal.

In some embodiments, the raw data memory device 220 may include any suitable volatile or non-volatile digital memory storage device. In some embodiments, the raw data memory 220 may also comprise communication electronics for transmitting raw digital ultrasound data to an external device over a wired or wireless network. In such cases, the transmitted raw echo data may be stored on the external device in any desired format. In other embodiments, the raw data memory 220 may include a combination of volatile memory, non-volatile memory and communication electronics.

In some embodiments, the raw data memory device 220 may comprise a temporary (volatile or non-volatile) memory section, and a long-term non-volatile memory section. In an example of such embodiments, the temporary memory may act as a buffer between the ADC and the beamformer in cases where the beamformer may be unable to operate fast enough to accommodate data at the full rate supported by the ADC.

In some embodiments, a long-term non-volatile memory device may be configured to receive data from a temporary memory device or directly from the ADC. Such a long-term memory device may be configured to store a quantity of raw echo data for subsequent processing, analysis or transmission to an external device.

In some embodiments, the quantity of data in the raw data memory may depend on the digital sampling rate, the size of each data sample (in bits or bytes), any data compression applied and other factors. Thus, as one example, a memory device with a capacity of about 16 GB may store raw echo data corresponding to about six seconds of real-time display (e.g., at a 25 MHz data sample rate, 16 bits per sample, 128 receive channels, 32 pings per frame, and 40 frames per second). In other embodiments, data representing a shorter or longer period of time may be stored in the same amount of memory.

In some embodiments, the beamforming block 232 and the image layer combining block 234 may each include any digital signal processing and/or computing components configured to perform the specified processes (e.g., as described below). For example, in various embodiments the beamforming 232 and image layer combining 234 may be performed by software running on a GPU or other computational accelerator, or by firmware running on an FPGA architecture. In various embodiments, some or all of the step of combining sub-images from elements of a common receive aperture to form first level image layers may be performed by either or both of the beamforming block 232 and the image layer combining block.

In some embodiments, the video processor 242 may include any video processing hardware, firmware and software components that may be configured to assemble image frames into a video stream for display and/or storage.

Real-Time Display and Initiating Raw Echo Data Capture

Figure 5:
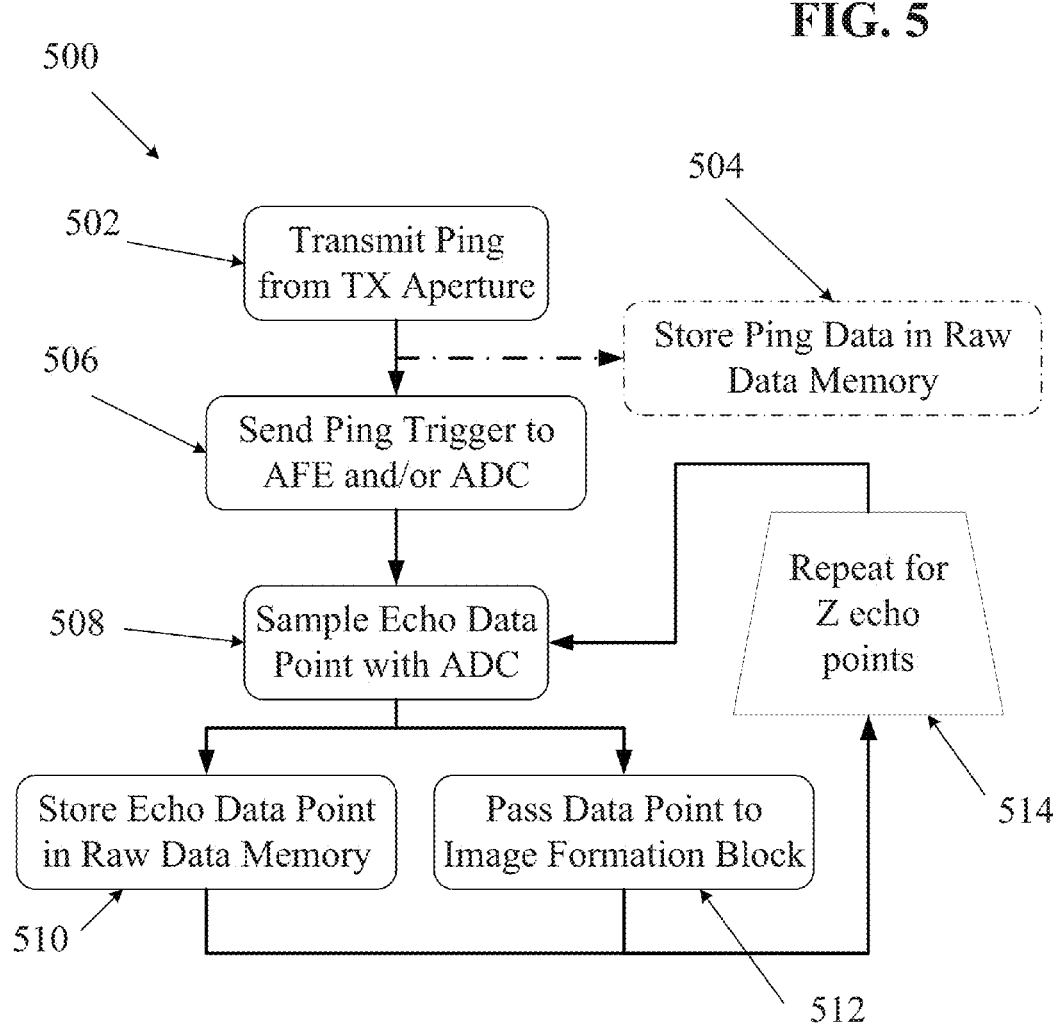
FIG. 5 is a process flow diagram illustrating one embodiment of a process for capturing and recording raw echo data.

With reference to the block diagram of FIG. 3 and the process flow diagram of FIG. 5, one embodiment of a process 500 for capturing and recording raw echo data will now be described. First, the transmit controller 204 may direct one or more transmit elements of the probe 202 to transmit an ultrasound ping 502. In some embodiments, the transmit controller 204 may also explicitly communicate 504 digital data about the transmitted ping (e.g., the identity of each transmit element being used for the ping, the magnitude of the ping, the duration of the ping, the frequency and specific waveform of the transmitted ultrasound signal, or other data) to the raw data memory 220. Nearly immediately after (or before) the transmit ping signal is sent, receive transducer elements of the probe 202 may begin receiving echoes and generating corresponding analog signals. In some embodiments, it may be desirable to wait for a time interval to elapse before collecting received data. In such embodiments, a 'begin capture' signal may be sent to the AFE 212 and/or the ADC 214 after any such time interval has elapsed. Such a time interval may be selected so as to only capture echo data from a desired depth range within the imaged object.

Upon receiving a ping trigger 506, the AFE 212 may begin amplifying and/or filtering received analog echo signals that are then passed to the ADC 214. The ADC 214 may then sample 508 the analog signals at regular intervals (e.g., 25 MHz in some embodiments, but at higher or lower rates depending on factors such as the frequency of the transmitted pings, the capabilities and precision of the interpolator and beamformer, and the need to maintain at least Nyquist-defined lower minimum sample rates in order to avoid frequency aliasing). Thus, at each sampling point, the ADC may generate a digital record containing a signal magnitude and a timestamp entry. This stream of digital records may then be recorded 510 in the raw data memory 202 for each sampled data point. In some embodiments, each data point may also be passed 512 to the image formation block 230. In some embodiments, the ADC 214 may be configured to store a fixed number of data points (e.g., as represented by variable 'Z' in FIG. 5). The process 500 of FIG. 5 may then be repeated 514 for any number of pings from any number of transmit apertures.

As indicated by the dotted line 250 in FIG. 3, in some embodiments digitized echo data may be sent directly from the ADC to the beamformer (in some cases after performing data conditioning steps, such as additional filtering, interpolation, down-sampling, up-sampling, etc.), and images may be beamformed, processed and displayed substantially in real-time with minimal latency. In some embodiments, in order to achieve such real-time display, any of various methods may be used to reduce the amount of processing needed to form images. For example, various data reduction methods may be used to minimize a human-perceptible latency between a user (e.g., a sonographer) changing the position of the probe and seeing the corresponding change displayed by the imaging system.

Figure 2:
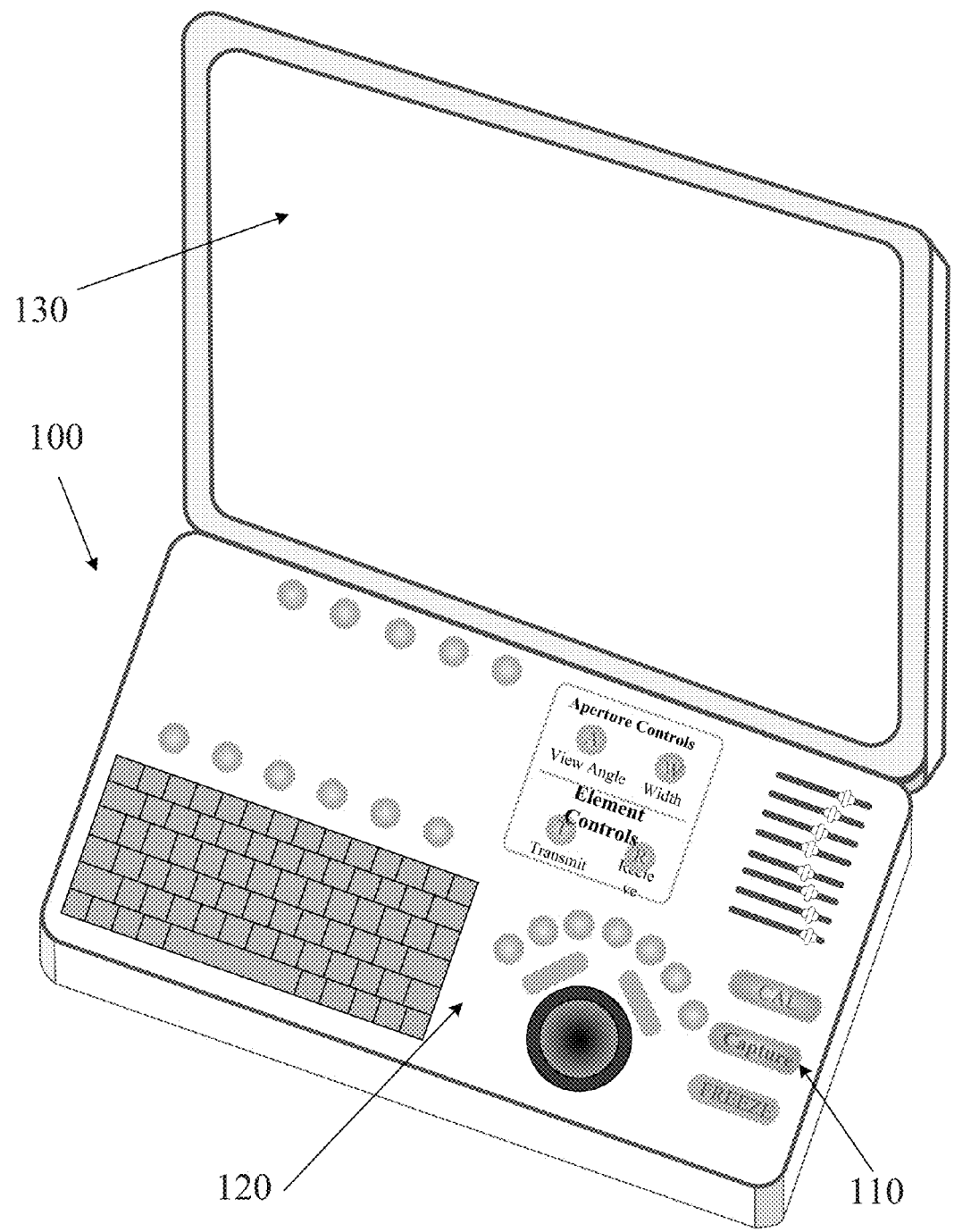
FIG. 2 is a perspective view illustration of one embodiment of an ultrasound imaging system control panel configured for capturing raw echo data.

In the embodiment of FIG. 2, a user may view an ultrasound image on a display screen 130 of a control panel 100 while moving the probe relative to the body being imaged. Once finding a desired view, the user may initiate a "capture" process on the ultrasound imaging control system. The system may then record some quantity of digitized raw echo data in a long term memory device. In some embodiments, a capture process may be initiated by pressing an appropriately purposed button 110 such as that illustrated in FIG. 2. In other embodiments, a capture process may be initiated through another user-interactive control 120, such as a touch-sensitive device, a dial, a slider, a retinal scanner, a voice command, a keyboard, a mouse, trackpad, touchpad, or a combination of user-interactive controls. In some embodiments, raw echo data capture may be initiated by remote control via a network connection.

In some embodiments, an ultrasound imaging system 200 may be configured to continuously store the most recent X seconds of raw echo data in either or both of a temporary memory device and/or a long-term memory device (also known as a "circular buffer"). For example, in some embodiments, the length of time 'X' for which raw echo data is continuously stored may depend on the capacity of the temporary memory device and or the long-term memory device, as well as the memory space needed to capture each fraction of a second of raw echo data. Thus, if the memory storage capacity is sufficient to store the most recent six seconds of raw echo data, then the system may be configured to continuously replace old data with new data in order to maintain a continuous store of the most recent six seconds of data. In other embodiments, the value of X may be a user-configurable or a predetermined time period less than or equal to the total capacity of the volatile and non-volatile memory.

In various embodiments, the "capture" process may be initiated retroactively or in advance. For example, in some embodiments a user may instruct the system (e.g., through a user interface interaction) to save the previous X seconds of data. Alternatively, the user may instruct the system to save the next X seconds of data. In further embodiments, a combination of retroactive and pre-active raw echo data may be captured and stored in a raw data memory device.

In some embodiments, raw echo data stored in the raw data memory device 220 may be retrieved and processed for real-time or near-real-time display of images. In other embodiments, raw echo data may be retrieved from a raw data memory device 220 and processed for playback in slow motion or fast motion (e.g., time-lapse) in order to see details not visible in real time.

For example, in one embodiment elements of a probe may be divided into two receive apertures, and eight transmit apertures. In this example embodiment, a single time-domain frame may be formed from echoes of eight pings transmitted from each of the eight transmit apertures received with elements of each of the first and second receive apertures. Thus, a single time-domain frame may be composed of a total of 16 second level image layers, (eight second-level image layers from each receive aperture). Alternatively, the number of time-domain frames may be increased (e.g., in order to create "slow motion" video) by forming each time-domain frame from a combination of a smaller number of second level images (e.g., eight second level images instead of 16). Conversely, the number of time-domain frames may be decreased (e.g., in order to create "time-lapse" video) by forming each time-domain frame from a combination of a greater number of second level images (e.g., 32 or 64 second level images instead of 16).

In another example, a probe may be divided into three receive apertures, and 16 transmit apertures. In this example embodiment, a single time-domain frame may be formed from echoes of 16 pings transmitted from each of the 16 transmit apertures received with elements of each of the first, second and third receive apertures. Thus, a single time-domain frame may be composed of a total of 48 second level image layers, (16 second-level image layers from each receive aperture). Alternatively, the number of time-domain frames may be increased (e.g., in order to create "slow motion" video) by forming each time-domain frame from a combination of a smaller number of second level images (e.g., eight or 24 second level images instead of 48). Conversely, the number of time-domain frames may be decreased (e.g., in order to create "time-lapse" video) by forming each time-domain frame from a combination of a greater number of second level images (e.g., 64 or 96 second level images instead of 48).

In other embodiments, some desired processing steps may require more processing time or computing power than may be available within time and hardware constraints of a live, real-time imaging session with an ultrasound imaging system. In such embodiments, raw echo data stored in the raw data memory device 220 of an ultrasound system may be retrieved and processed for later display of images.

For example, in some embodiments echo data may be re-processed and displayed hours, days, weeks, months, or even years after a patient-present ultrasound data capture session. In some embodiments, subsequent processing and display may occur on entirely different hardware, firmware and/or software from the system used to capture the ultrasound echo data—processing may even take place on cloud-based distributed systems, for example, with the resultant images streamed to mobile devices such as wireless tablets, smart phones, or other internet-connected display systems. Additionally, as new processing algorithms and heuristic visualization and/or optimization methods become available, previously-captured data may be re-processed to view further details.

Capture to External Storage

In some embodiments, raw echo data that is captured and stored in a raw data memory device as described above may subsequently be copied or forwarded to an external (e.g., a backup) memory storage device. Such data transmissions may take place over any available wired or wireless data transfer system, such as Bluetooth, IR/Infra-Red, USB, IEEE 1394 Firewire, Thunderbolt, Ethernet/Intranet/Internet (TCP/IP, FTP, etc.) or others. In some embodiments, the data may be loaded back onto an ultrasound imaging system (e.g., the same system used for insonification and raw echo data capture or a similarly-configured ultrasound imaging system) for re-processing, re-beamforming and image viewing. In other embodiments, a personal computer may be configured with software and/or hardware to beamform and/or process the raw echo data without the use of a dedicated ultrasound imaging system. In other embodiments, raw echo data may be beamformed, processed and displayed by software on any other suitably configured computational device or system, such as a tablet or smart phone. In other embodiments, raw echo data may be uploaded over a network to a network-accessible server which may process image data remotely.

Figure 4:
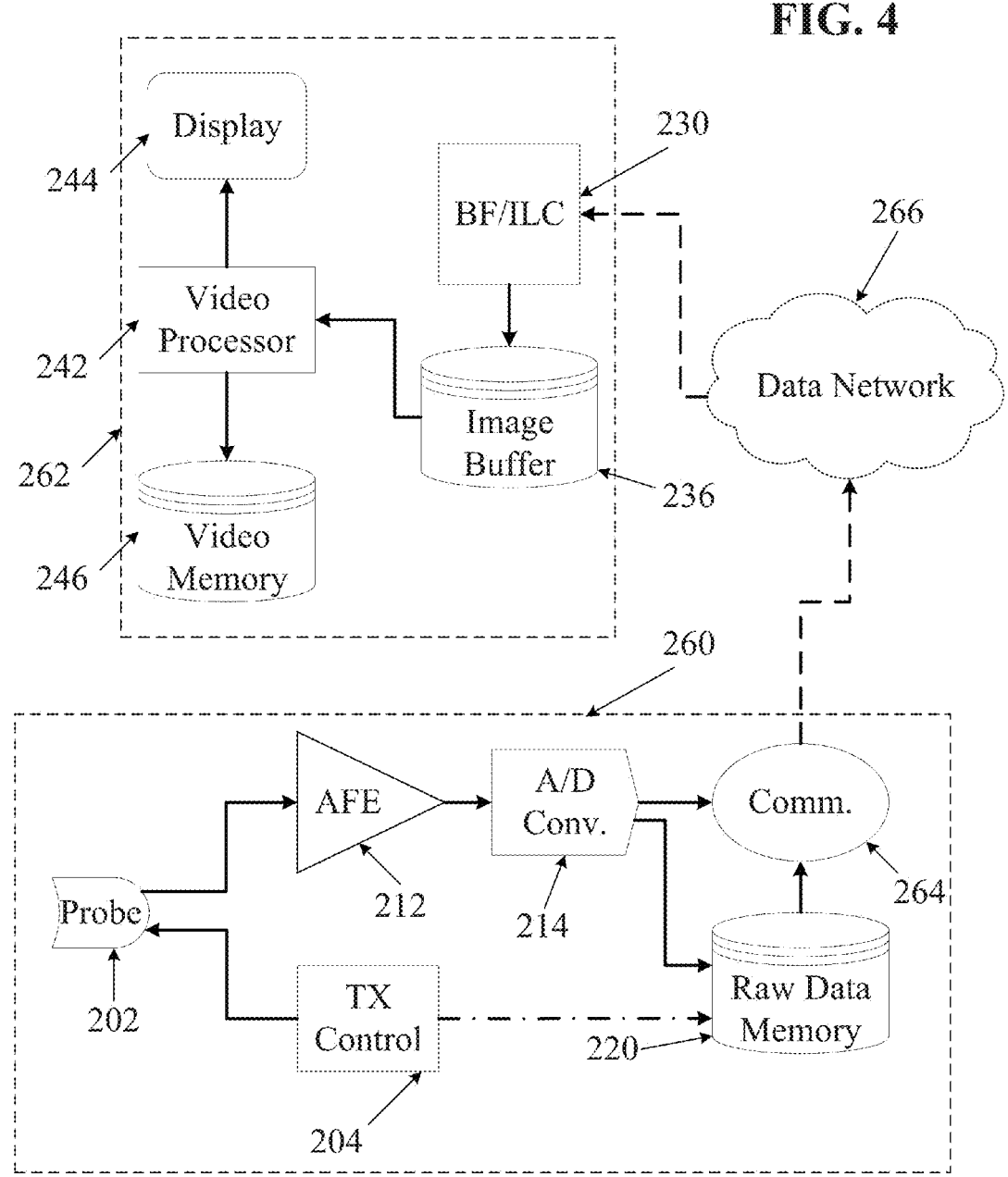
FIG. 4 is a block diagram illustrating several functional components of one embodiment of an ultrasound imaging system configured for remote raw echo data capture.

FIG. 4 illustrates an embodiment of an ultrasound data capture & transmission device 260 that may be configured with minimal hardware components for communication of raw echo data to a remote imaging system 262 via a communications device 264 and a wired or wireless network 266. The ultrasound data capture device 260 of FIG. 4 may include a transmit controller 204, an AFE 212 and an ADC 214 as described above. In place of any beamforming or image processing components, the device 260 may instead include a communications device 264 configured to transmit raw echo data to a remote system 262 via a network 266. The remote system 262 may include hardware, firmware and software configured to beamform and process the raw echo data captured by the device 260. In some embodiments, the communications device may be configured to stream raw echo data in real time to the remote system. In other embodiments, the ultrasound data capture device 260 may include an internal memory device 220 for short term storage of raw echo data (e.g., as a transmission buffer). In other embodiments, an internal memory device 220 may be configured for longer term storage of raw echo data within the capture device 260. For example, in some embodiments, the internal raw data memory device 220 may comprise a removable data storage device such as an SD card, an optical storage device (such as a CD or DVD) or any other solid state non-volatile digital memory device.

For example, in one embodiment, a patient may visit a sonographer and the sonographer may conduct an ultrasound examination during which raw echo data is captured and stored. Hours, days or weeks later (i.e., any time after the session, even long after patient is physically present), a physician may use a personal computer or an imaging system to re-examine images produced during the examination session. In some embodiments, such re-examination may include several processes that are only possible with access to raw echo data. Examples of such processes will now be described.

In some embodiments, raw data from an imaging session may be stored along with raw echo data captured while imaging a calibration phantom. Raw echo data of a phantom imaging session may be used for later calibration of the imaging session data by correcting transducer element position assumptions made during beamforming. Information describing the position of each transducer element may be obtained by a calibration process as described in Applicants' prior applications. Such element position data may be stored in a calibration memory device 220, which may be physically located with other electronics, or may be located in a remote network-accessible server. However, in some embodiments, the element-position information may change between performing a calibration operation and capturing raw ultrasound data. For example, a probe may be dropped, damaged or may be otherwise altered before or during a raw echo data capture session. In some embodiments, the ability to re-process stored raw echo data means that a probe may actually be re-calibrated after raw echo data is captured, and the data may be re-beamformed using the updated element position information. In other embodiments, raw echo data stored in a raw data memory device may be analyzed to determine that a probe is actually out of calibration.

Re-Processing Raw Echo Data

Some embodiments of ultrasound imaging systems with a raw data memory may enable many unique user interactions that may dramatically extend the diagnostic usefulness of ultrasound imaging. By capturing and storing raw echo data during an imaging session, such ultrasound imaging systems may allow a user to adjust fundamental beamforming and image processing settings to obtain dramatically improved images and/or alternate views or details using only the stored raw echo data.

In some embodiments, stored raw echo data may be re-beamformed at any time after the raw echo data has been captured. As described above, beamforming in the context of multiple aperture ultrasound imaging using a ping transmission system is generally the process of determining a display location for each reflector based on trigonometric relationships between the reflector, the location of a transmit element, and the location of a receive element. Such trigonometric relationships are determined based on a distance calculation using an assumed speed-of-sound and the time interval between a transmitted ping and a received echo for a given reflector. Thus, the display location of any given reflector may be determined by several factors, each of which may be dependent on several other factors. During normal real-time imaging, constant values for some or all of these factors may be assumed in order to limit processing time. When processing time is not constrained by the need to display images in real time, the variable factors that go into beamforming calculations or other image formation and/or image processing steps may be adjusted or optimized to further improve image quality. Thus, during time-shifted re-beamforming of raw echo data, potentially variable quantities such as the speed of sound and the locations of transmit or receive elements may be optimized to improve image quality.

The ability to re-beamform ultrasound data may also facilitate an improved ability to "zoom in" on a desired region of an image without losing any image resolution. This may be understood with an analogy to digital photography. Many digital cameras have an "optical zoom" function and a "digital zoom" function. The "optical zoom" optically gives the impression of bringing the subject closer to the camera, thereby increasing the size of the image. As a result, the "optically zoomed" image benefits from the full pixel resolution of the camera's image capture device. By contrast, the "digital zoom" merely crops the image and increases the size of the captured pixels, thereby giving the impression of the same "zoom" result, but at the expense of reduced image resolution with each incremental "digital zoom" step. In contrast to the resolution-losing "zoom" process employed by most ultrasound imaging systems, an ultrasound imaging system with a pre-beamformer memory device may provide the ability to zoom in without losing image resolution. The ability to zoom in and re-beamform ultrasound image data within a smaller area than an original image is analogous to an "optical zoom" because the beamformer may produce a full-resolution image from only the image data within a desired "zoomed-in" region of the image.

Generating ultrasound images using a multiple aperture ping imaging process means that images from an entire region of interest are "in focus" at all times. This is true because each transmitted ping illuminates the entire region, and receive apertures receive echoes from the entire region. In such cases, the maximum extent of the image may be primarily limited by attenuation and signal-to-noise factors rather than by the confined focus of transmit or receive beamforming apparatuses. As a result, a full-resolution image may be formed from any portion of an insonified region of interest using the same set of raw echo data. The term "image window" will be used herein to refer to a portion of the entire insonified region of interest that is to be beamformed and displayed. Therefore, in various embodiments, an image window may be changed by zooming or panning from one image window to another. In some embodiments, simultaneous images may be formed of multiple overlapping or non-overlapping image windows within the insonified region.

By contrast, using a phased array transmit/receive imaging system, the only imaged region in focus is the region within the depth range at which the transmitted ultrasound signals are focused. As a result, such systems (even if they were to employ a pre-beamformer memory) are limited in their ability to construct images of portions of the insonified region other than those originally displayed during a real-time imaging session. Furthermore, when users of such systems wish to increase the size of the displayed image by "zooming in", the system typically interpolates data in between displayed pixels, because additional sample data is not available to fill in those gaps otherwise.

For example, during a typical imaging session, a user of an ultrasound system using a multiple aperture ping imaging process may select an image area of any desired "zoom" level so as to display an image of a selected portion of the entire insonified region. In some embodiments, raw echo data from any part of a region approximately the same width as a multiple aperture ultrasound probe may be beamformed to produce an image. During such an imaging session, the system may capture and store raw echo data of the entire insonified region while displaying a real-time image of only the selected region. In order to generate the real-time image, the system may perform the receive beamforming steps described above using received (and/or stored) echo data. In particular, the system may triangulate received echoes using an assumed speed-of-sound value, element position data, time delays of received echoes and a coherent/incoherent summation algorithm to form an image. In some embodiments, the system may form a real-time image with a pixel resolution optimized for a particular display. In doing so, in the case of display devices with native resolutions lower than the actual beamformed resolution, some echo data representing points between the displayed image pixels may be ignored. In some embodiments, hardware limitations, such as limits imposed by processing or data transmission electronics, may necessitate using less than all available echo data when beamforming for real-time display. For these reasons or others, under some circumstances, a system may be limited to using only a portion of all available echo data for forming an image.

If, at some point after the imaging session, it becomes desirable to zoom in or out (or to pan the image horizontally or vertically) to get a different view of some portion of the originally insonified area, a user may simply define a new view area anywhere within that region. The system may then beamform the echo data representing echoes within the selected region by triangulating the echoes using an assumed speed-of-sound value, element position data, time delays of received echoes and a coherent/incoherent summation algorithm to form new image pixels of only the selected region. In doing so, the new image may be formed with the full beamforming resolution, even if the selected region was not visible in the original real-time image. As discussed elsewhere herein, when producing an image from stored raw echo data, the various beamforming parameters (speed-of-sound, element positions, weighting factors, summation algorithms, etc.) may also be changed relative to values used during a real-time imaging session. As a result, a somewhat lower level of skill may be acceptable for capturing raw data during a real-time imaging session.

In one embodiment, a process of ultrasound imaging using stored raw echo data may comprise the steps of, during an ultrasound imaging session, using an ultrasound system configured for multiple aperture ping imaging, generating a real-time image of a first section of a region of interest while storing echo data from an entire insonified region. The echo data may then later be retrieved from the memory device, and a second image of a second region of interest may be generated using the same or different beamforming parameters. The second image may have the same, lower, or higher pixel resolution as the first image. In some cases, the second region of interest may be a smaller area within the first region of interest. In other embodiments, a portion of the second region of interest may lie outside of the first region of interest, but within the insonified region. In still other embodiments, the first and second regions of interest may be entirely non-overlapping.

In some embodiments, the ability to independently beamform separate sections of a single insonified region may be beneficially used to simultaneously view two separate portions of the insonified region. As described elsewhere herein, several seconds, minutes or more of image data may be stored and retrieved for later viewing. In some embodiments, a first region of interest may be defined to include a first anatomical structure such as a cross-section of substantially an entire heart of a patient, while a second region of interest may be defined to include a zoomed-in region of the first region in order to increase the image size of a portion or sub-structure of the anatomical structure, such as an aortic valve of the heart. Because both images are generated from the same data set, the moving images of the structure and the sub-structure (e.g., the heart and the valve) will be perfectly synchronized and may be viewed simultaneously to visualize the action of different regions of the heart (or other structure) at the same point in the cardiac cycle (or other movement of the anatomical structure). Similarly, a third image may also be produced to show simultaneous action of another portion of the insonified region, highlighting another sub-structure or an entirely separate structure, such as the tricuspid valve of the heart or an adjacent organ. The same techniques may be used to view regions of other organs (e.g., lungs, liver, kidneys, or muscular-skeletal structures such as wrist joints, ankle joints, knee joints, shoulder joints, hip joints or a spine).

If based on 3D volumetric data (as described below), perfectly synchronized image windows may even be defined for structures that do not lie on a common plane. Therefore, first and second image windows covering non-coplanar segments of a common three-dimensional volume may be extracted from a stored echo dataset, and those image windows may be independently beamformed and displayed simultaneously in synchronicity.

In another embodiment, a system may be configured to produce an image with a pixel resolution much higher than a display resolution by beamforming all available echo data of a complete insonified region at a maximum possible resolution. In such embodiments, a maximum resolution of beamformed images may be determined by evaluating echo data to establish the size of the smallest reasonably-discernible details, and then beamforming the echo data to form an image in which those small details are visible. In some embodiments, assuming sufficient hardware resources and time are available, the maximum resolution using all available echo data may be limited only by the total aperture width and the wavelength of ultrasound transmitted and received. In some such embodiments, an image may be formed in which a single pixel represents a physical area the size of approximately half the wavelength of the ultrasound signals used. In some embodiments, such high resolution images may be combined as frames in a video loop.

In other embodiments, the above methods of zooming into regions of an image may allow for very accurate measurements of anatomical or structural features within an insonified region. Measurements are made possible by the fact that, at any chosen "zoom" level, the relationship between pixel size and imaged object size is known exactly as a result of the pixel-oriented beamforming method described above. For example, regardless of what zoom level was displayed during real-time imaging, if a feature is within the insonified region and included in an echo data set, a user may later zoom in to view and accurately measure features such as artery diameter, vein diameter, heart chamber size, fetal heart size or any other desired feature or object.

As described above, in some embodiments image layers formed from different pings or from different receive apertures may be combined using various combinations of coherent and incoherent summation in order to accommodate speed-of-sound differences across a large total aperture, or to improve the image resolution or speckle reduction in the combined image. In some embodiments, further coherent and incoherent summation algorithms may be applied to stored raw echo data in order to seek a different result.

In some embodiments, weighting factors may be applied to various pixels during image layer combining in order to improve image quality as described in applicants' prior application (U.S. patent application Ser. No. 13/850,823, titled "Systems and Methods for Improving Ultrasound Image Quality by Applying Weighting Factors" filed on Mar. 26, 2013). By re-processing stored raw echo data, such weighting factors may be applied differently, or may be further optimized after data has been captured.

Some embodiments are described above in which assumed values for the speed-of-sound along one or more ultrasound transmit and/or receive paths may be adjusted or optimized in order to improve the alignment of combined image layers. In some embodiments, such adjustments and/or optimizations may be applied to stored raw echo data. Applying such adjustments during re-processing of stored raw echo data may allow for more time-consuming optimizations to be performed (e.g., optimizing an average speed-of-sound value to use in beamforming calculations).

In some embodiments, transmit and receive apertures may be re-defined after ultrasound data has been captured. As described above, the size, location and number of transmit or receive apertures may be changed depending on a particular target object geometry or other factors. In some embodiments, such changes in the size, location or number of apertures of may be made adaptively in order to optimize the quality of an image produced from stored raw echo data.

Applicants' prior application (U.S. patent application Ser. No. 13/730,346, filed Dec. 28, 2012, titled "M-Mode Ultrasound Imaging of Arbitrary Paths") describes systems and methods for defining and displaying an arbitrary M-mode path. Using stored raw echo data, new M-mode paths may be defined and displayed based on stored raw echo data that has been re-beamformed during a raw data viewing session. In some embodiments, an m-mode path may be defined in one field of view, and may be displayed along with a completely different field of view that does not necessarily contain the same feature as the M-mode path. For example, in some embodiments raw echo data corresponding to points along the m-mode path may be retrieved from a raw data memory device and beamformed independent of raw echo data used to form a complete image.

Doppler imaging and Elastographic imaging involve transmit patterns that are not necessarily present during all multiple aperture ping imaging sessions. For example, ping-based Doppler ultrasound imaging involves transmitting relatively low frequency pings (compared to an imaging frequency) from one or two transmit apertures at a very high ping repetition rate (e.g., nearly or faster than a rate corresponding to a round trip ping travel time). Ping-based elastographic imaging may also involve transmitting imaging pings at a very high ping repetition rate following transmission of a shear-wave inducing pulse.

When such patterns are transmitted, resulting raw echo data may be captured and stored, whether or not the echoes are processed to display Doppler or Elastography results during the initial imaging session. Thus, in some embodiments, when multiple aperture Doppler or Elastography transmit patterns described in the above-referenced applications are present during a raw echo data capture session, Doppler or Elastography results may be interpreted or analyzed using the captured raw echo data retrieved from a raw data memory device. For example, in some embodiments, multiple aperture Doppler patterns may be transmitted during an imaging session, and the resulting Doppler echo data may be captured and stored without processing or displaying color flow Doppler during the live imaging session. The stored raw echo data may be later retrieved from memory and processed using the same or different processing hardware in order to visualize and analyze the results of the Doppler imaging. Similarly, in some embodiments, multiple aperture Elastography patterns may be transmitted during an imaging session, and the resulting echo data may be captured and stored without processing or displaying strain information during the live imaging session. The stored raw echo data may be later retrieved from memory and processed using the same or different processing hardware in order to visualize and analyze the results of the Elastography process.

In some embodiments, image data may be compressed in order to produce real-time images without significant perceptible delay. In some cases, such compression may have the effect of combining images obtained at different points in time (e.g., by combining image layers obtained from multiple transmitted pings). This may have the effect of reducing an actual displayed frame rate from a maximum possible frame rate at which echo data is captured. However, by re-beamforming raw echo data and combining images differently, a much higher frame rate (i.e., a higher number of frames per second) may be achieved. In some embodiments, images formed at the much higher frame rate may be viewed frame-by-frame or in slow motion While slow motion playback may occur at a lower number of frames per second relative to a display frame rate, because such frames may represent events that occurred at shorter time intervals compared with images presented for real-time viewing, more detail may be seen. For example, some movements of portions of a heart valve occur much faster than can be captured with traditional ultrasound systems. The ability to view images of such motion at a much higher frame-capture rate may enable dramatic improvements to diagnostic capabilities.

In addition to the re-processing of raw echo data, any other downstream image or video processing steps may be re-applied, modified or improved after re-processing raw echo data. For example, various video processing filters (e.g., mean, median, squaring, Gaussian, despeckle, highpass, edge enhancement, contrast enhancement, unsharp masking or other image and video processing filters) may be re-applied after re-processing raw echo data into image and video data.

Embodiments of Capturing and Using Three-Dimensional Raw Data

Raw data of three-dimensional volumes may also be beneficially captured, stored, and re-beamformed using similar systems and methods. The same ping-based imaging techniques described above may be applied to 3D volumetric data by transmitting ping signals that are not constrained to a single plane (e.g., three-dimensional semi-spherical or near-semi-spherical ultrasound signals), and receiving echoes with receive elements displaced from one another along at least two orthogonal axes perpendicular to the imaged medium. Multiple aperture ultrasound probes configured for ping-based 3D volumetric imaging may have large total apertures, which may be substantially greater than any expected coherence width for an intended imaging application.

3D volumetric data may be captured and stored using substantially the same systems and methods described above. Typically, a multiple aperture probe for 3D imaging may have substantially more transducer elements than a probe intended primarily for 2D imaging. As such, an imaging system for capturing and storing 3D volumetric data during a ping-based imaging process may include substantially more receive channels and may also include a larger capacity raw data memory device. The raw echo data stored in the memory device may be structured as described above, such that echoes may be distinguished based on the particular receive element that received them and the particular transmitted ping that generated the echoes.

Beamforming 3D ping-based echo data may also be performed using similar systems and methods to those used for beamforming 2D ping-based echo data. Each digitized sample value may represent a scatterer from the insonified region of interest. As in the 2D case, the amplitude of each received sample along with its time of arrival and the exact positions of the transmitting and receiving transducers may be analyzed to define a locus of points identifying potential positions of the scatterer. In the 3D case, such a locus is a three-dimensional ellipsoid having as its foci the positions of the transmit and receive transducers. Each unique combination of transmit and receive transducer elements may define a separate view of the same reflector. Thus, by combining information from multiple transmit-receive transducer combinations, the actual location of each reflector may be more accurately represented.

For example, in some embodiments an image in a 3D array of voxels may be assembled in computer memory by beginning with an evaluation of a selected digital sample. The selected digitized sample value may be written into every voxel indicated by the corresponding ellipsoid described above. Proceeding to do the same with every other collected sample value, and then combining all resulting ellipsoids may produce a more refined image. Real scatterers are indicated by the intersection of many ellipsoids whereas parts of the ellipsoids not reinforced by other ellipsoids will have low levels of signal and may be treated as noise (i.e., eliminated or reduced by filters or other image processing steps).

In other embodiments, the order of computation may be changed by beginning with a selected voxel in a final 3D image volume to be produced. For example, for a selected voxel, the closest stored sample may be identified for each transmitter/receiver pair. All samples corresponding to the selected voxel (i.e., all samples with an ellipsoid that intersects the voxel) may then be evaluated and summed (or averaged) to produce a final representation of the voxel. Closeness of a sample to a selected voxel may be determined by calculating the vector distance from the three-dimensional position of a transmitter (i.e., the transmitter from which the ping signal was transmitted to produce the echo sample) to the selected voxel position plus the vector distance from the selected voxel position to the position of a receiver at which the sample was received. Such a linear distance may be related to the time-divided sample values by dividing the total path length by speed of sound through the imaged object. Using such a method, the samples corresponding to a calculated time may be associated with the selected voxel.

Because ping signals insonify an entire region to be imaged, echo data obtained via ping-based imaging is seamless. By contrast, 2D images assembled from a series of scanlines typically require some amount of interpolation of image data in spaces in between adjacent scanlines. Similarly, volumetric data assembled from a series of planar slices also tend to require some amount of interpolation of image data in spaces in between adjacent planar slices.

The seamless nature of ping-based echo data means that arbitrary 2D slices may be taken through any portion of a 3D volume without the need for interpolation. In some cases, non-planar or curved slice may be taken through a section of volumetric data, and the result of the curved-path slice may be displayed on a two-dimensional display, either as a flattened planar image or as a perspective drawing. Such information may also be presented via a three-dimensional display such as a holographic display or a stereoscopic display. Therefore, in some embodiments, raw echo data from a volumetric imaging session may be retrieved from a memory device, some or all of the volume may be beamformed and displayed as an image, a desired region of the volume may be selected (automatically by software or manually by an operator), and the selected region may be re-beamformed and presented as a new image.

Figure 6:
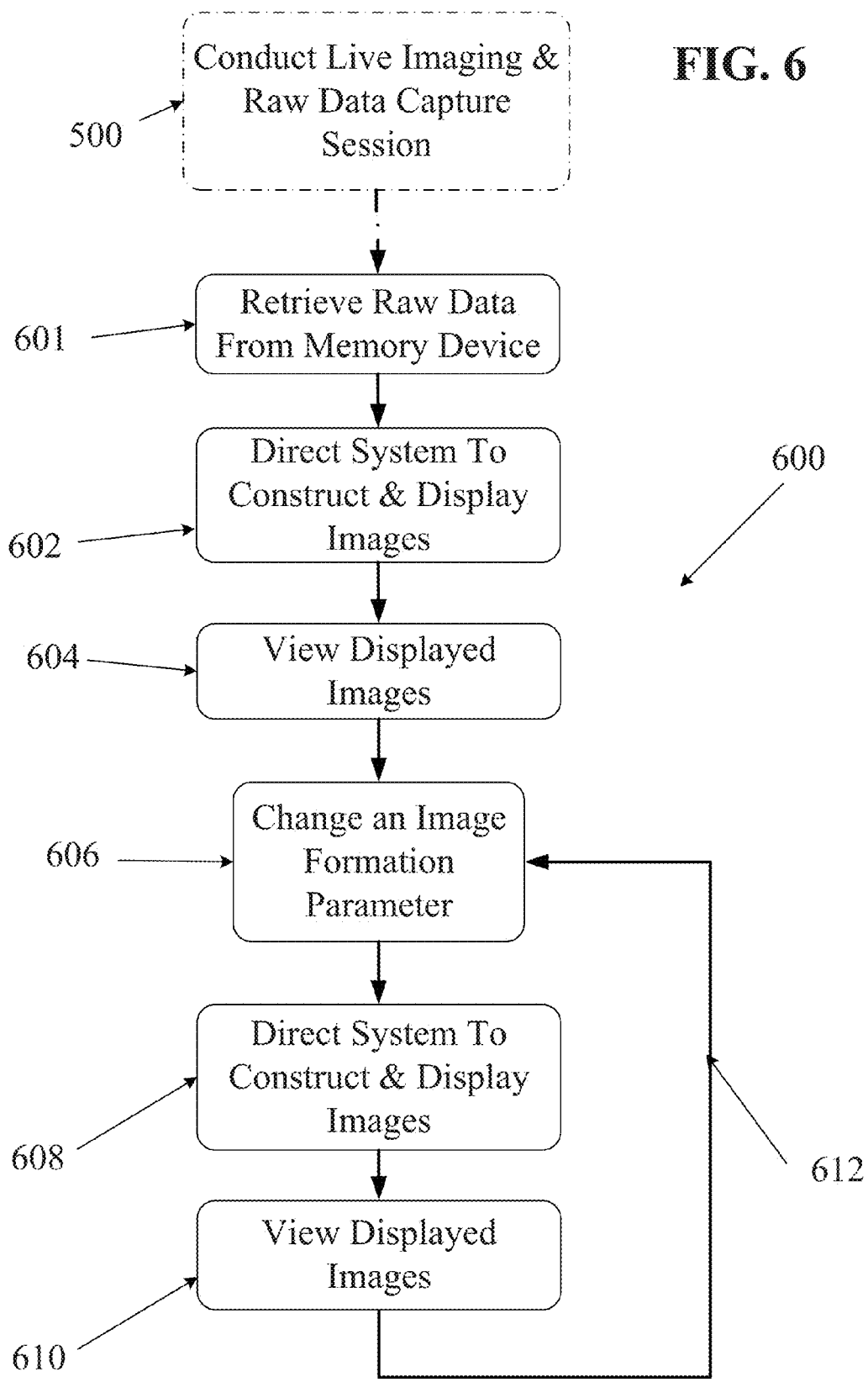
FIG. 6 is a process flow diagram illustrating an embodiment of a process by which a practitioner may utilize raw echo data captured during a prior live imaging session.

FIG. 6 illustrates a process 600 by which a practitioner may use a suitably configured imaging system to examine raw echo data captured during a live imaging session 500 that may have been performed by the same practitioner or a different practitioner at a previous time and/or in a different location. Raw data from the imaging session may be retrieved from a memory device 601, the practitioner may direct the system to construct images 602 from the raw data using a predetermined set of image formation parameters, and the practitioner may then view the resulting images 604. The practitioner may then change one or more image formation parameters 606 in an attempt to improve the image or to change a portion of the insonified region to view (e.g., changing an image window by zooming in, zooming out, or panning). The practitioner may then direct the system to construct and display images using the changed parameters 608, and may then view the new images 610. The steps of changing image formation parameters 606, constructing images using the changed parameter(s) 708 and displaying new images 610 may be repeated 612 as many times as desired.

Figure 7:
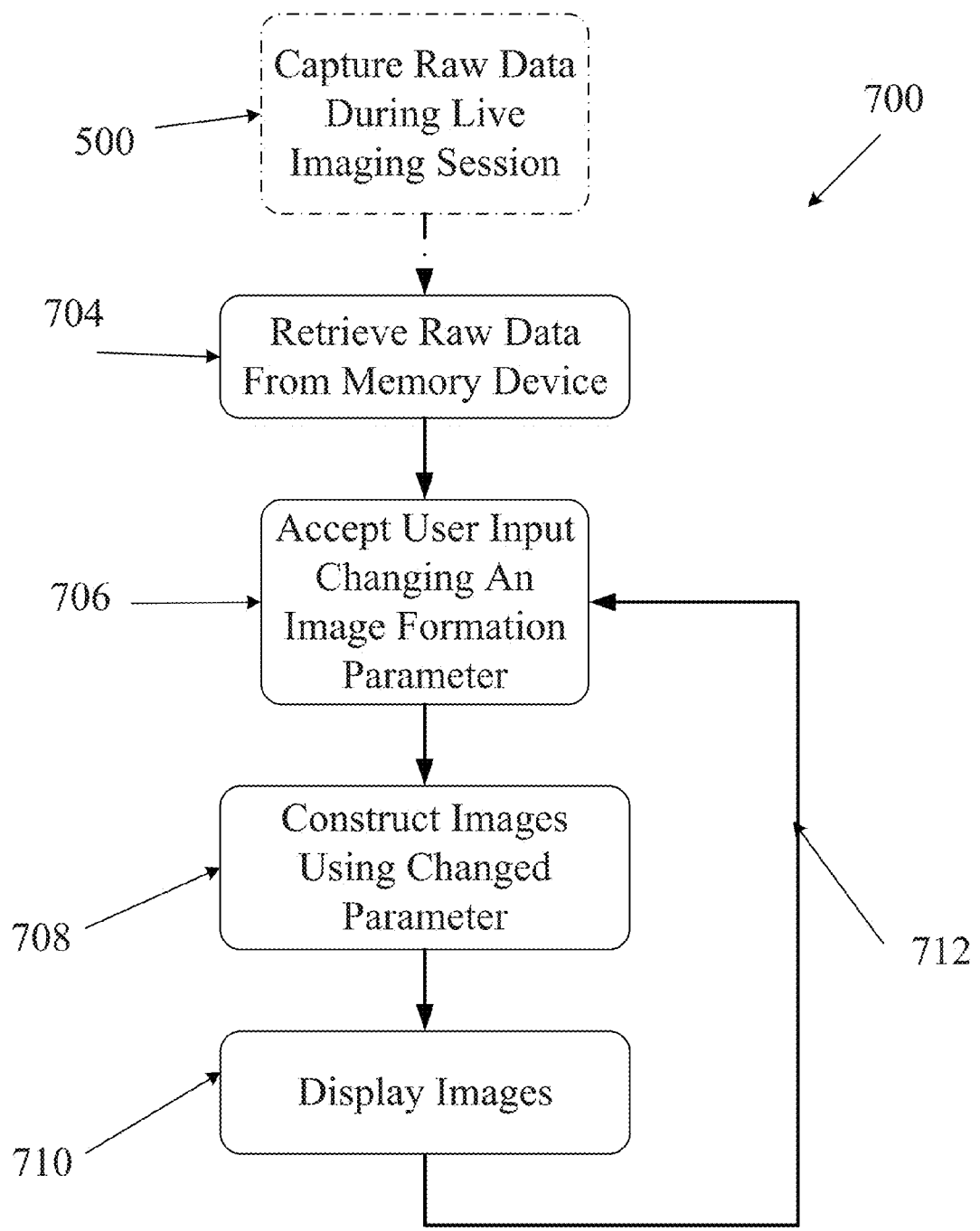
FIG. 7 is flow diagram illustrating an embodiment of a process by which an imaging system may process and display raw echo data captured during a prior live imaging session.

FIG. 7 illustrates a process 700 that may be performed by a suitably configured ultrasound imaging system in order to re-process raw ultrasound echo data captured during a live imaging session 500. The process 700 may include retrieving the raw data from a memory device 704, accepting user input indicating one or more image formation parameters to be changed 706, constructing images using the changed image formation parameter(s) 708, and displaying the new image(s) 710. The steps of accepting user input 706, constructing images using the changed parameter(s) 708 and displaying new images 710 may be repeated 712 as many times as desired. As described in various embodiments above, the user input may explicitly specify the image formation parameters to be changed, or the user input may implicitly indicate image formation parameters to be changed. An example of an explicit parameter to change may include changing a speed of sound value, while an example of an implicitly specified parameter may include a selection of an image layer combination algorithm that combines image layers using a combination of coherent and incoherent addition.

In either the process 600 of FIG. 6 or the process 700 of FIG. 7, the changed image formation parameters may include beamforming parameters, such as a speed of sound value, one or more transducer element position variables, or a weighting factor. Image formation parameters may also include a grouping of transducer elements into apertures, or image layer combining parameters such as changing a number of image layers per frame or an algorithm for combining image layers at different levels using coherent or incoherent addition. Changing image parameters may also include selecting an M-mode line to display, or selecting a two-dimensional slice from a three-dimensional volume.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the commonly used phrase "and/or." Thus, for example the phrase "A or B may be blue" may mean any of the following: A alone is blue, B alone is blue, both A and B are blue, and A, B and C are blue. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A method of producing an image from ultrasound data, comprising the steps of:
    retrieving a first data set from a first non-volatile digital memory device with a computing system, the first data set comprising data describing first transmitter coordinates of one or more transmit elements making up a transmit aperture;
    retrieving a second data set from a second non-volatile digital memory device with the computing system, the second data set comprising a first series of ultrasound echo strings produced by the transmit aperture, each ultrasound echo string of the first series comprising a plurality of echo samples received by one of a plurality of receive elements of a first receive aperture;
    retrieving a third data set from the first non-volatile digital memory device with the computing system, the third data set comprising data describing coordinates of each of the plurality of elements of the first receive aperture relative to a common coordinate system with the first transmitter coordinates;

retrieving a fourth data set from the second non-volatile digital memory device with the computing system, the fourth data set comprising a second series of ultrasound echo strings produced by the transmit aperture, each ultrasound echo string of the second series comprising a plurality of echo samples received by one of a plurality of receive elements of a second receive aperture;

retrieving a fifth data set from the first non-volatile digital memory device with the computing system, the fifth data set comprising data describing coordinates of each of the plurality of elements of the first receive aperture relative to the common coordinate system;

obtaining a transmit location of the transmit aperture from the first data set in the computing system;

obtaining receive element coordinates for each of the plurality of elements of the first receive aperture from the second data set in the computing system;

obtaining receive element coordinates for each of the plurality of elements of the second receive aperture from the fifth data set in the computing system;

receiving, from a user input device, user input defining a first set of beamforming parameters, at least one parameter of the first set of beamforming parameters having a value different than a value used during an imaging session in which the second and fourth data was captured;

beamforming, with a beamfon ling processor, the second data set to determine a pixel display location for each echo sample in each echo string of the first series of ultrasound echo strings using the first set of beamforming parameters, the transmit location, and the receive element coordinates for each of the plurality of receive elements of the first receive aperture to determine trigonometric relationships between the transmit aperture, reflectors, and the receive elements of the first receive aperture and the receive elements of the second receive aperture to produce a first set of complete two-dimensional sub-images of a target object in the computing system;

combining, with an image layer combining processor, the first set of complete two-dimensional sub-images of the target object to form a first combined image;

beamforming, with the beamforming processor, the fourth data set to determine a pixel display location for each echo sample in each echo string of the second series of ultrasound echo strings using the first set of beamforming parameters, the transmit location, and the receive element coordinates for each of the plurality of receive elements of the second receive aperture to determine trigonometric relationships between the transmit aperture, reflectors, and the receive elements of the first receive aperture and the receive elements of the second receive aperture to produce a second set of complete two-dimensional images of the target object in the computing system;

combining, with the image layer combining processor, the second set of complete two-dimensional sub-images of the target object to form a second combined image;

combining, with the image layer combining processor, the first combined image and the second combined image to form a third combined image of the target object; and displaying the third combined image of the target object on a display.

2. The method of claim 1, further comprising:
after displaying the first set of images of the target object on the display, adjusting at least one beamforming parameter to form a second set of beamforming parameters different than the first set of beamforming parameters; and
beamforming the second data set using the second set of beamforming parameters to produce a second set of images of the target object.

3. The method of claim 2, wherein the at least one beamforming parameter is a speed-of-sound in the target object.

4. The method of claim 2, wherein the at least one beamforming parameter is an adjusted position of a transmit transducer element of the transmit aperture or a receive transducer element of the receive aperture relative to the common coordinate system.

5. The method of claim 2, wherein the at least one beamforming parameter is a weighting factor.

6. The method of claim 1, further comprising:
after displaying the first set of images of the target object on the display, defining a second image window of the target object different than a first image window of the first set of images; and
beamforming the second data set to produce a second set of images of the second image window of the target object.

7. The method of claim 6, wherein the image window covers an area within the first set of images and less than a total area of the first set of images, the method further comprising measuring a size of a structure visible in the second set of images.

8. The method of claim 1, further comprising adding a m-mode line to a display based on an image formed from the second data set.

9. The method of claim 1, further comprising adjusting an algorithm for combining images coherently and incoherently.

10. The method of claim 1, wherein producing the first set of images further comprises combining a first plurality of image layers to form a first set of frames, each image layer corresponding to a different combination of the transmit aperture and the receive aperture, and displaying the first set of frames at a first frame rate.

11. The method of claim 10, further comprising beamforming the second data set to produce a second set of images of the target object, including combining a second plurality of image layers to form a second set of frames, each image layer corresponding to a different combination of the transmit aperture and the receive aperture, the second set of frames having a greater number of frames than the first set of frames, and displaying the second set of frames at a second frame rate that is higher than the first frame rate.

* * * * *